(12) United States Patent
Johnson et al.

(10) Patent No.: US 11,574,731 B2
(45) Date of Patent: Feb. 7, 2023

(54) COMPUTER-BASED SYSTEMS AND METHODS FOR ACTION ITEM EVALUATION AND INITIATION VIA TASK DATA OBJECT GENERATION

(71) Applicant: Optum, Inc., Minnetonka, MN (US)

(72) Inventors: Scott D. Johnson, Wayzata, MN (US); Mallory B. Van Horn, Oklahoma City, OK (US); Michael B. Wentzien, Chanhassen, MN (US)

(73) Assignee: Optum, Inc., Minnetonka, MN (US)

( * ) Notice: Subject to any disclaimer, the term of this patent is extended or adjusted under 35 U.S.C. 154(b) by 184 days.

(21) Appl. No.: 16/904,313

(22) Filed: Jun. 17, 2020

(65) Prior Publication Data

US 2021/0398657 A1    Dec. 23, 2021

(51) Int. Cl.
| | | |
|---|---|---|
| *G16H 40/20* | (2018.01) | |
| *G06F 9/48* | (2006.01) | |
| *G06Q 10/10* | (2012.01) | |
| *G16H 50/20* | (2018.01) | |
| *G06Q 10/06* | (2012.01) | |
| *G16H 10/60* | (2018.01) | |
| *H04L 67/1097* | (2022.01) | |
| *G06F 3/0482* | (2013.01) | |

(52) U.S. Cl.
CPC ............ *G16H 40/20* (2018.01); *G06F 9/485* (2013.01); *G06Q 10/06316* (2013.01); *G06Q 10/10* (2013.01); *G16H 10/60* (2018.01); *G16H 50/20* (2018.01); *G06F 3/0482* (2013.01); *H04L 67/1097* (2013.01)

(58) Field of Classification Search
CPC ........ G16H 40/20; G16H 10/60; G16H 50/20; G06F 9/485; G06F 3/0482; G06Q 10/06316; G06Q 10/10; H04L 67/1097

USPC .......................................................... 705/2–3
See application file for complete search history.

(56) References Cited

U.S. PATENT DOCUMENTS

| | | |
|---|---|---|
| 7,464,041 B2 | 12/2008 | Merkin et al. |
| 8,290,786 B2 | 10/2012 | Ika et al. |
| (Continued) | | |

FOREIGN PATENT DOCUMENTS

WO    00/69331 A1    11/2000

OTHER PUBLICATIONS

Beaulah, Simon et al. "AI In Quality Measurement," 2018 Linguamatics, Ltd., (57 pages). [Retrieved from the Internet Jun. 23, 2020] <https://www.ncqa.org/wp-content/uploads/2018/11/Workgroup-1B_Artificial-Intelligence_20181114.pdf>.

*Primary Examiner* — Michael Tomaszewski
(74) *Attorney, Agent, or Firm* — Alston & Bird LLP

(57) ABSTRACT

To identify relevant action items (that may ultimately be reflected as claims data) for closing an identified gap in care reflected by combinations of disparate claims data records within a claims data store, a task-based interventional system executes rule-based models to determine action items eligible for closing a particular gap in care identified based on criteria associated with one or more programs. The task-based interventional system executes one or more machine-learning models to generate care scores associated with relevant entities associated with the identified gaps in care and generates a task data object comprising data indicative of an action item to close the gap in care together with executable jobs for initiating computer-based workflows to provide data indicative of the gap in care to relevant entities.

18 Claims, 13 Drawing Sheets

(56) References Cited

U.S. PATENT DOCUMENTS

| | | |
|---|---|---|
| 8,898,798 B2 | 11/2014 | Rogers et al. |
| 9,501,624 B2 | 11/2016 | Vishnubhatla et al. |
| 10,242,416 B2 | 3/2019 | Thesman |
| 10,262,112 B2 | 4/2019 | Ryan |
| 10,262,756 B2 | 4/2019 | Ghouri et al. |
| 10,395,330 B2 | 8/2019 | Dorris et al. |
| 2009/0024414 A1 | 1/2009 | Mansour et al. |
| 2014/0164010 A1 | 6/2014 | Roy et al. |
| 2014/0330621 A1 | 11/2014 | Nichols et al. |
| 2015/0019248 A1* | 1/2015 | Anand .................. G06F 40/40 705/2 |
| 2016/0357909 A1 | 12/2016 | Northam et al. |
| 2016/0357910 A1* | 12/2016 | Ghouri .................. G16H 10/60 |
| 2017/0185723 A1 | 6/2017 | McCallum et al. |
| 2018/0261330 A1 | 9/2018 | Saripalli |
| 2018/0286509 A1 | 10/2018 | Shah et al. |
| 2018/0350461 A1* | 12/2018 | Anderson .............. G06Q 10/10 |
| 2019/0043606 A1 | 2/2019 | Roots et al. |
| 2019/0087395 A1 | 3/2019 | Priestas et al. |
| 2021/0313063 A1* | 10/2021 | Holub .................. G06N 7/005 |

* cited by examiner

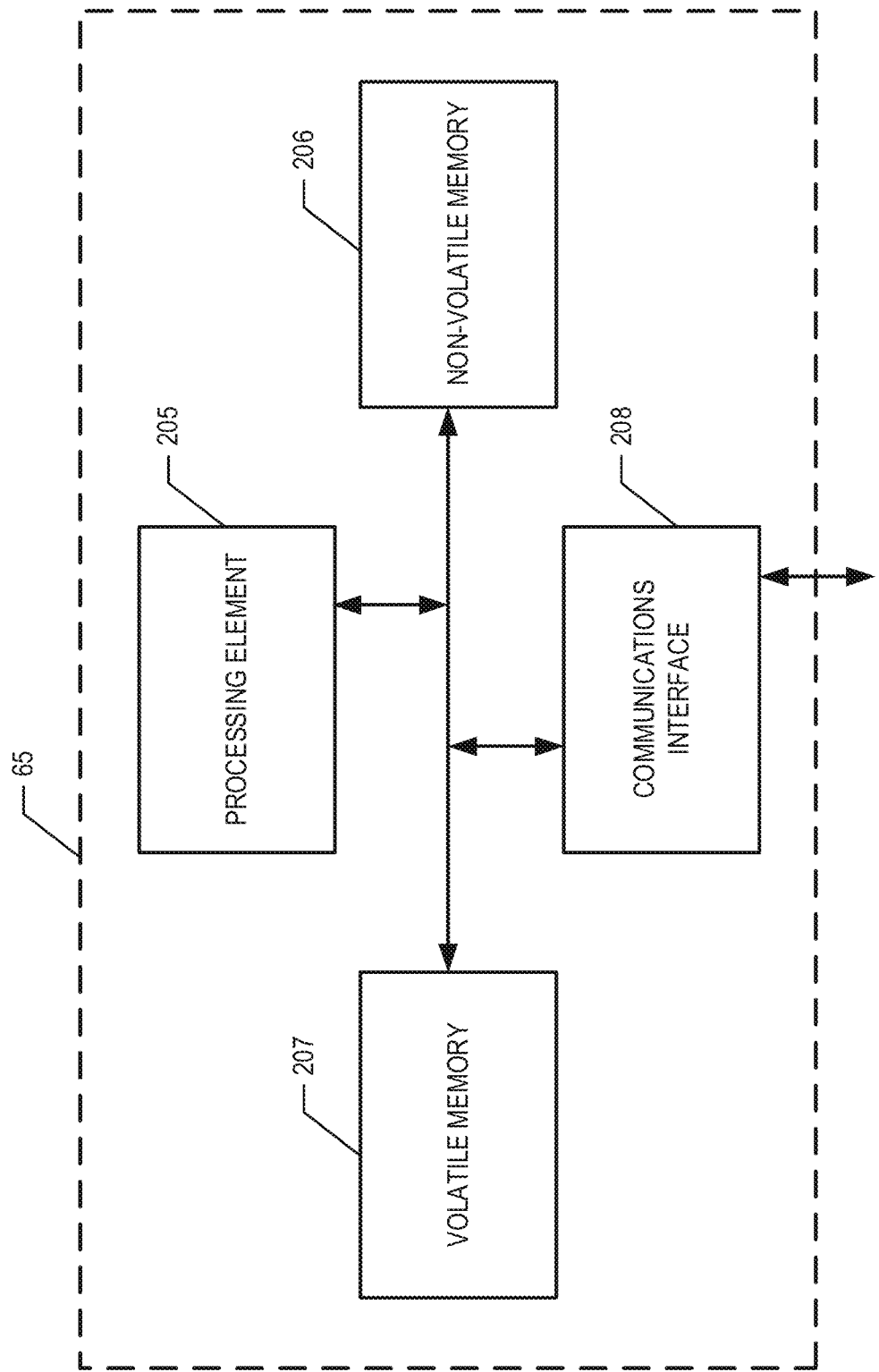

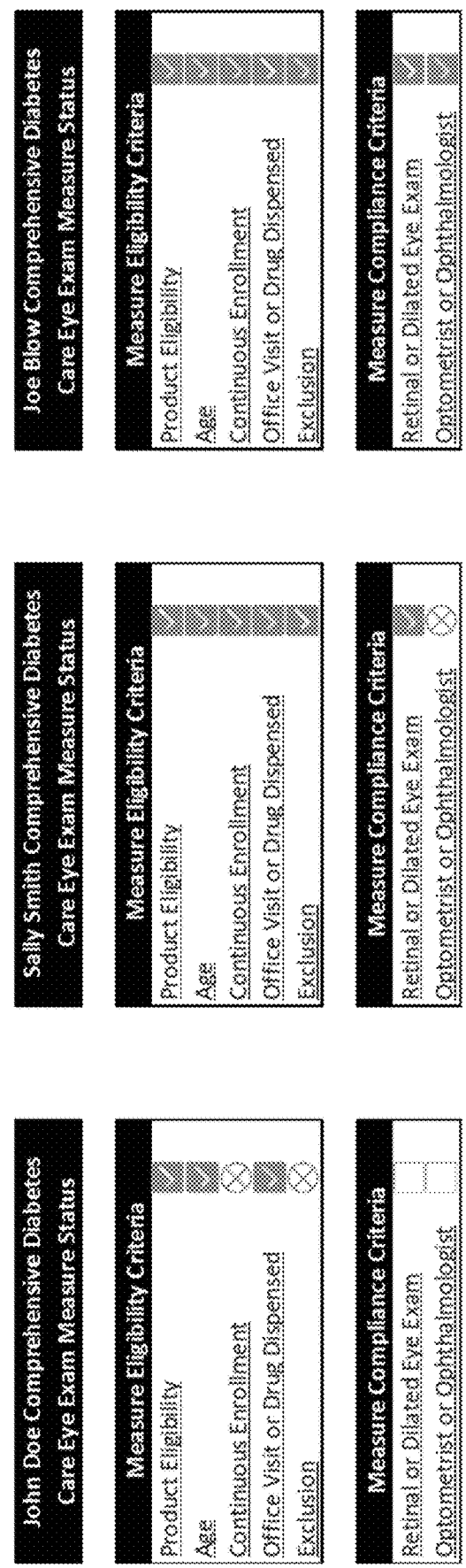

| Member ID | Member Name | Provider | Provider Group | Care Score |
|---|---|---|---|---|
| 123456789 | John Doe | Dr. Wentzien | West Medical | 2.5 |
| 987654321 | Sally Smith | Dr. Johnson | Care Partners | 1.7 |
| 345678102 | Joe Blow | Dr. Chennisi | East Medical | 1.3 |
| 432567098 | Ralph Jones | Dr. Wentzien | West Medical | 0.8 |
| 345876234 | Peter Larson | Dr. Wentzien | West Medical | 0.7 |
| 432175689 | Susan Ramon | Dr. Chennisi | East Medical | 0.3 |

Calculate Member Care Score

FIG. 8A

| Provider | Provider Group | CMS Contract | Measure | Care Score |
|---|---|---|---|---|
| Dr. Wentzien | West Medical | H1234 | C01 | 3.5 |
| Dr. Johnson | West Medical | H1234 | C01 | 1.3 |
| Dr. Chennisi | West Medical | H1234 | C01 | 2.7 |
| Dr. Wentzien | West Medical | H1234 | C02 | 3.5 |
| Dr. Johnson | West Medical | H1234 | C02 | 1.3 |
| Dr. Chennisi | West Medical | H1234 | C02 | 2.7 |

Calculate Provider Care Score

FIG. 8B

| CMS Contract | Measure | Intervention | Care Score |
|---|---|---|---|
| H1234 | C01 | Mailer | 0.1 |
| H1234 | C01 | Telephonic | 0.5 |
| H1234 | C01 | Housecall | 2.3 |
| H1234 | C01 | Provider | 3.4 |
| H9876 | C01 | Mailer | 0.2 |
| H9876 | C01 | Telephonic | 0.7 |
| H9876 | C01 | Housecall | 2.5 |
| H9876 | C01 | Provider | 0.8 |

Calculate Payer Care Score

FIG. 8C

| Member ID | Member Name | Measure(s) | Intervention | Provider | Provider Group | Care Score |
|---|---|---|---|---|---|---|
| 123456789 | John Doe | C01, C02 | Provider | Dr. Wentzien | West Medical | 2.5 |
| 987654321 | Sally Smith | C01, C02, C03 | Housecall | Payer | | 1.7 |
| 345678102 | Joe Blow | C02 | Provider | Dr. Chennisi | East Medical | 1.3 |
| 432567098 | Ralph Jones | C03 | Provider | Dr. Wentzien | West Medical | 0.8 |
| 345876234 | Peter Larson | C04 | Telephonic | Payer | | 0.7 |
| 432175689 | Susan Ramon | C05 | Mailer | Payer | | 0.3 |

Next best intervention list

FIG. 9

COMPUTER-BASED SYSTEMS AND METHODS FOR ACTION ITEM EVALUATION AND INITIATION VIA TASK DATA OBJECT GENERATION

BACKGROUND

Computational evaluations of various action items, particularly as they relate to individual persons, have historically been limited in determining an overall expected effectiveness of communicating and/or otherwise requesting execution of a particular action item. Moreover, workflow systems and/or other computational action item evaluation solutions have historically been incapable of utilizing information regarding an aggregate evaluation of an overall desired goal to determine best action items to take on an individualized basis.

Accordingly, a need exists for improved systems and methods for automatically evaluating and determining appropriate action items for inclusion within one or more workflow systems.

BRIEF SUMMARY

Various embodiments provide task-based interventional systems configured for executing both rule-based and machine-learning based evaluation modules for identifying, based at least in part on data inputs, one or more available action items for attaining a particular goal and for identifying a most-appropriate mechanism through which to initiate a determined action item (e.g., by generating a workflow object for submission to a workflow system, for providing a notification to a particular actor to request execution of an action item, and/or the like). In certain embodiments, a task-based interventional system provided in accordance with embodiments as discussed herein may be particularly suitable for evaluating gaps in care relating to a patient's medical care, and for determining one or more methods through which to close any identified gaps in care, without requiring substantial human interactions for estimating how best to contact a patient, provider, and/or payer to close a particular gap in care.

Various embodiments are directed to a computer-implemented task-based interventional system, the task-based interventional system comprising: one or more non-transitory memory storage areas; one or more processors configured to: receive claims data relating to a patient, wherein the claims data comprises a plurality of claim data objects each identifying previously executed actions and at least one program; based at least in part on the at least one program, apply a rule-based criteria for determining whether the claims data relating to the patient reflects one or more gaps in care relating to the at least one action program, wherein each of the one or more gaps in care are reflected as unfulfilled action items that are not satisfied by the plurality of claim data objects; output, from the rule-based criteria, criteria for closing the one or more gaps in care; execute one or more machine-learning models to generate care scores for one or more available action items to close the one or more gaps in care; identify, via the one or more machine-learning models, an action item to close the one or more gaps in care; generate a task data object for initiation of the action item, wherein the task data object comprises: at least one actor identifier indicating a communication address of an individual for executing at least a portion of the action item; a desired actor-based action item comprising a human-readable indication of an action item; an interventional strategy comprising at least one computer-based communication protocol for providing communication between the task-based interventional system and the communication address; and an executable job for execution at least partially by the task-based interventional system; and execute the executable job to provide at least a portion of the task data object to an external computing entity.

In certain embodiments, executing one or more machine-learning models to generate care scores comprises: evaluating historical data corresponding to each of a plurality of actors to generate a care score corresponding to each of the plurality of actors indicating a likelihood of each of the plurality of actors to complete assigned action items. Moreover, the one or more processors may be further configured to generate a user interface providing a populated listing of gaps in care relating to each of at least one program. In certain embodiments, executing the executable job comprises causing a workflow software system to populate a workflow data object. Moreover, in certain embodiments, executing the executable job comprises transmitting at least a portion of the task data object to an external computing entity via the interventional strategy. In various embodiments, identifying an action item to close a gap in care comprises: generating care scores for each of a plurality of entities; and determining the action item via a machine-learning model based at least in part on generated care scores for each of the plurality of entities. In certain embodiments, generating care scores for a plurality of entities comprises: determining a patient care score based at least in part on historical data indicative of historical actions of the patient; determining a provider care score for a relevant care provider associated with the patient, wherein the provider care score is determined based at least in part on historical data associated with the relevant care provider; and determining a payer care score indicative of one or more interventional strategies historically implemented by a payer associated with the patient.

Certain embodiments are directed to a computer-implemented method for generating a computer-based intervention to close gaps in care in stored claims data. The method may comprise: receiving, via one or more processors, claims data relating to a patient, wherein the claims data comprises a plurality of claim data objects each identifying previously executed actions and at least one program; based at least in part on the at least one program, applying, via the one or more processors, a rule-based criteria for determining whether the claims data relating to the patient reflects one or more gaps in care relating to the at least one action program, wherein each of the one or more gaps in care are reflected as unfulfilled action items that are not satisfied by the plurality of claim data objects; generating, via the one or more processors, output from the rule-based criteria, criteria for closing the one or more gaps in care; executing, via the one or more processors, one or more machine-learning models to generate care scores for one or more available action items to close the one or more gaps in care; identifying, via the one or more processors executing the one or more machine-learning models, an action item to close the one or more gaps in care; generating, via the one or more processors, a task data object for initiation of the action item, wherein the task data object comprises: at least one actor identifier indicating a communication address of an individual for executing at least a portion of the action item; a desired actor-based action item comprising a human-readable indication of an action item; an interventional strategy comprising at least one computer-based communication protocol for providing communication between the task-based interventional system and the communication address; and an executable job for execution at least partially by the task-based interventional system; and executing, via the one or more processors, the executable job to provide at least a portion of the task data object to an external computing entity.

In certain embodiments, executing one or more machine-learning models to generate care scores comprises: evaluating historical data corresponding to each of a plurality of actors to generate a care score corresponding to each of the plurality of actors indicating a likelihood of each of the plurality of actors to complete assigned action items. In various embodiments, the method further comprises generating a user interface providing a populated listing of gaps in care relating to each of at least one program. In various embodiments, executing the executable job comprises causing a workflow software system to populate a workflow data object. In certain embodiments, executing the executable job comprises transmitting at least a portion of the task data object to an external computing entity via the interventional strategy. In various embodiments, identifying an action item to close a gap in care comprises: generating care scores for each of a plurality of entities; and determining the action item via a machine-learning model based at least in part on generated care scores for each of the plurality of entities. In various embodiments, generating care scores for a plurality of entities comprises: determining a patient care score based at least in part on historical data indicative of historical actions of the patient; determining a provider care score for a relevant care provider associated with the patient, wherein the provider care score is determined based at least in part on historical data associated with the relevant care provider; and determining a payer care score indicative of one or more interventional strategies historically implemented by a payer associated with the patient.

Certain embodiments are directed to a non-transitory computer-readable storage medium having program code embedded thereon, the program code executable on a processor of a computer system to perform processes for: receiving claims data relating to a patient, wherein the claims data comprises a plurality of claim data objects each identifying previously executed actions and at least one program; based at least in part on the at least one program, applying a rule-based criteria for determining whether the claims data relating to the patient reflects one or more gaps in care relating to the at least one action program, wherein each of the one or more gaps in care are reflected as unfulfilled action items that are not satisfied by the plurality of claim data objects; generating output from the rule-based criteria, criteria for closing the one or more gaps in care; executing one or more machine-learning models to generate care scores for one or more available action items to close the one or more gaps in care; identifying, via the one or more machine-learning models, an action item to close the one or more gaps in care; generating a task data object for initiation of the action item, wherein the task data object comprises: at least one actor identifier indicating a communication address of an individual for executing at least a portion of the action item; a desired actor-based action item comprising a human-readable indication of an action item; an interventional strategy comprising at least one computer-based communication protocol for providing communication between the task-based interventional system and the communication address; and an executable job for execution at least partially by the task-based interventional system; and executing the executable job to provide at least a portion of the task data object to an external computing entity.

In certain embodiments, executing one or more machine-learning models to generate care scores comprises: evaluating historical data corresponding to each of a plurality of actors to generate a care score corresponding to each of the plurality of actors indicating a likelihood of each of the plurality of actors to complete assigned action items. In various embodiments, the non-transitory computer-readable storage medium further comprises executable portions configured for generating a user interface providing a populated listing of gaps in care relating to each of at least one program. In various embodiments, executing the executable job comprises causing a workflow software system to populate a workflow data object. In certain embodiments, executing the executable job comprises transmitting at least a portion of the task data object to an external computing entity via the interventional strategy. Moreover, in certain embodiments, identifying an action item to close a gap in care comprises: generating care scores for each of a plurality of entities; and determining the action item via a machine-learning model based at least in part on generated care scores for each of the plurality of entities. In certain embodiments, generating care scores for a plurality of entities comprises: determining a patient care score based at least in part on historical data indicative of historical actions of the patient; determining a provider care score for a relevant care provider associated with the patient, wherein the provider care score is determined based at least in part on historical data associated with the relevant care provider; and determining a payer care score indicative of one or more interventional strategies historically implemented by a payer associated with the patient.

BRIEF DESCRIPTION OF THE SEVERAL VIEWS OF THE DRAWINGS

Reference will now be made to the accompanying drawings, which are not necessarily drawn to scale, and wherein:

FIG. 2A is a schematic of a task-based interventional system in accordance with certain embodiments of the present invention;

FIGS. 6A-6B provide example outputs of HEDIS engines in accordance with certain embodiments;

FIGS. 8A-8C illustrate example provider-specific care scores generated in accordance with various embodiments; and FIG. 9 illustrates example care scores provided in accordance with a listing of next-best action items.

DETAILED DESCRIPTION

Figure 1:
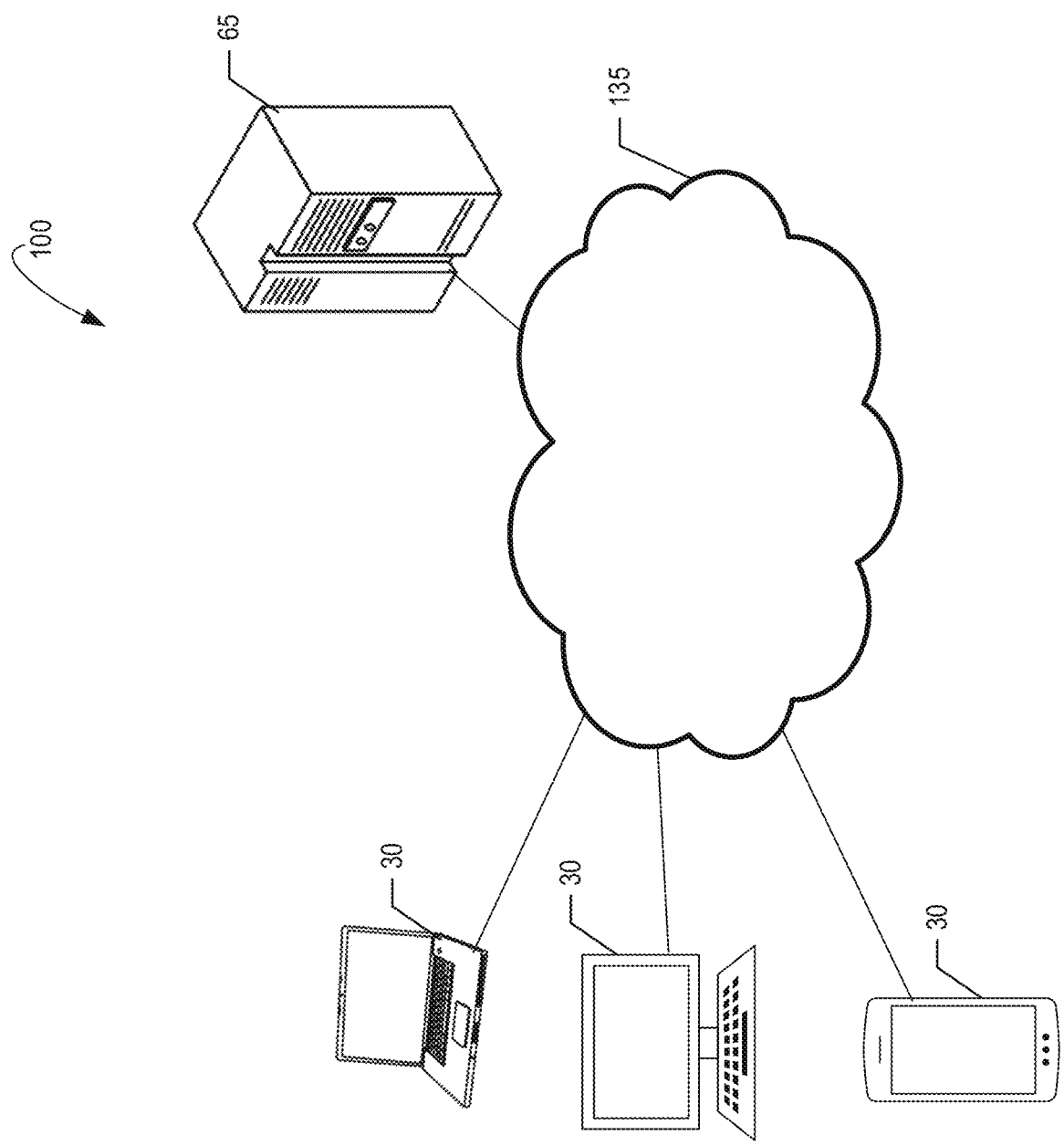
FIG. 1 is a diagram of a system that can be used in conjunction with various embodiments of the present invention.

The present disclosure more fully describes various embodiments with reference to the accompanying drawings. It should be understood that some, but not all embodiments are shown and described herein. Indeed, the embodiments may take many different forms, and accordingly this disclosure should not be construed as limited to the embodiments set forth herein. Rather, these embodiments are provided so that this disclosure will satisfy applicable legal requirements. Like numbers refer to like elements throughout.

I. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magneto resistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

II. EXEMPLARY SYSTEM ARCHITECTURE

FIG. 1 provides an illustration of a system 100 that can be used in conjunction with various embodiments of the present invention. As shown in FIG. 1, the system 100 may comprise one or more task-based interventional system 65, one or more user computing entities 30 (e.g., which may encompass handheld computing devices, laptop computing devices, desktop computing devices, and/or one or more Internet of Things (IoT) devices, and/or the like, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Task-Based Interventional System

FIG. 2A provides a schematic of a task-based interventional system 65 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the task-based interventional system 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. For instance, the task-based interventional system 65 may communicate with other computing entities, one or more user computing entities 30, and/or the like.

As shown in FIG. 2A, in one embodiment, the task-based interventional system 65 may include or be in communication with one or more processing elements 205 (also referred to as processors, processing circuitry, and/or similar terms used herein interchangeably) that communicate with other elements within the task-based interventional system 65 via a bus, for example, or network connection. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the task-based interventional system 65 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 206 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, metadata repositories database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably and in a general sense to refer to a structured or unstructured collection of information/data that is stored in a computer-readable storage medium.

Memory media 206 (e.g., metadata repository) may also be embodied as a data storage device or devices, as a separate database server or servers, or as a combination of data storage devices and separate database servers. Further, in some embodiments, memory media 206 may be embodied as a distributed repository such that some of the stored information/data is stored centrally in a location within the system and other information/data is stored in one or more remote locations. Alternatively, in some embodiments, the distributed repository may be distributed over a plurality of remote storage locations only. An example of the embodiments contemplated herein would include a cloud data storage system maintained by a third-party provider and where some or all of the information/data required for the operation of the system may be stored. As a person of ordinary skill in the art would recognize, the information/data required for the operation of the system may also be partially stored in the cloud data storage system and partially stored in a locally maintained data storage system.

Figure 2B:
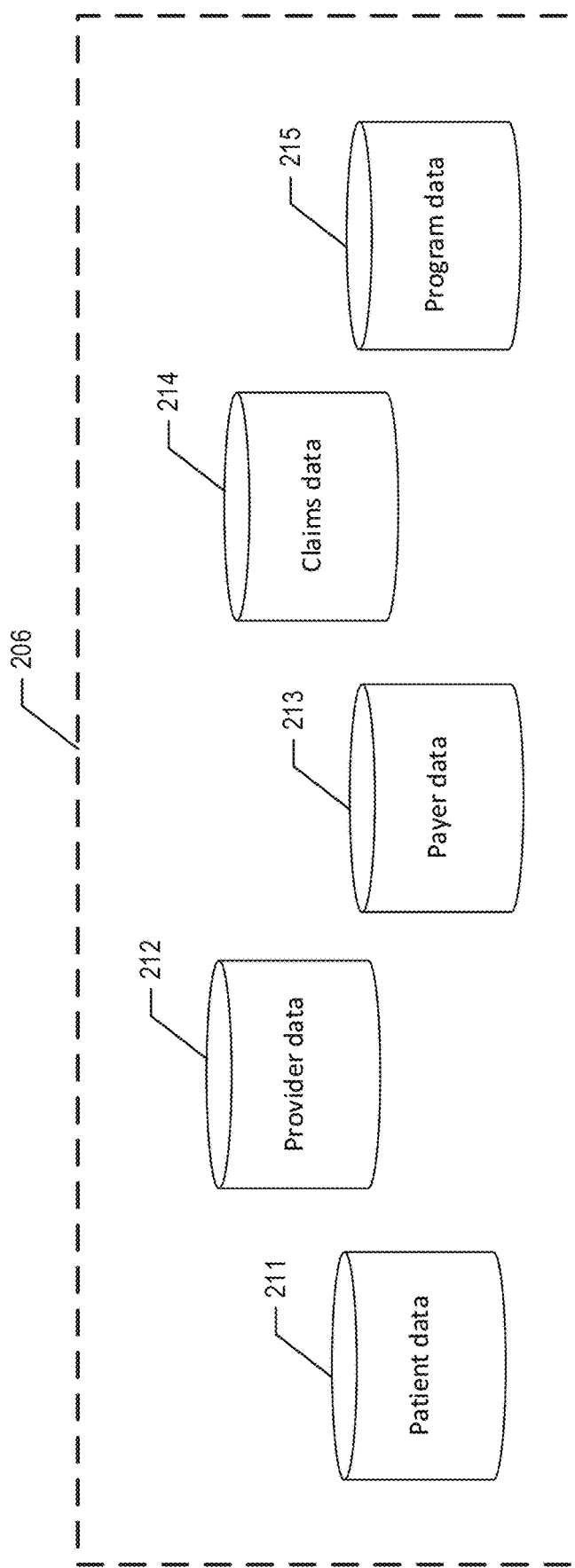
FIG. 2B is a schematic representation of a memory media storing a plurality of data assets.

Memory media 206 (e.g., metadata repository) may include information/data accessed and stored by the system to facilitate the operations of the system. More specifically, memory media 206 may encompass one or more data stores configured to store information/data usable in certain embodiments. For example, as shown in FIG. 2B, the memory media 206 may be embodied as one or more data storage areas (e.g., within a single centralized location or distributed among a plurality of disparate storage locations), and may comprise a plurality of data storage repositories, such as patient data storage area 211 (e.g., configured for storing patient data, such as patient profiles as discussed herein), a provider data storage area 212 (e.g., storing provider data, such as provider profiles as discussed herein), a payer data storage area (e.g., storing payer data, such as payer profiles as discussed herein), a claims data storage area (e.g., storing claims data as discussed herein), program data storage area 215 (e.g., storing data regarding various program requirements/criteria for eligibility and/or compliance of particular programs). Data stored within such data repositories may be utilized during operation of various embodiments as discussed herein.

In one embodiment, the task-based interventional system 65 may further include or be in communication with volatile media (also referred to as volatile storage, memory, memory storage, memory circuitry and/or similar terms used herein interchangeably). In one embodiment, the volatile storage or memory may also include one or more volatile storage or memory media 207 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the task-based interventional system 65 with the assistance of the processing element 205 and operating system.

As indicated, in one embodiment, the task-based interventional system 65 may also include one or more network and/or communications interfaces 208 for communicating with various computing entities (e.g., user computing entities 30), such as by communicating data, content, information, and/or similar terms used herein interchangeably that can be transmitted, received, operated on, processed, displayed, stored, and/or the like. For instance, the task-based interventional system 65 may communicate with computing entities or communication interfaces of other computing entities, user computing entities 30, and/or the like. In this regard, the task-based interventional system 65 may access various data assets.

As indicated, in one embodiment, the task-based interventional system 65 may also include one or more network and/or communications interfaces 208 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the task-based interventional system 65 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol. The task-based interventional system 65 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), Hypertext Markup Language (HTML), and/or the like.

As will be appreciated, one or more of the task-based interventional system's components may be located remotely from other task-based interventional system 65 components, such as in a distributed system. Furthermore, one or more of the components may be aggregated and additional components performing functions described herein may be included in the task-based interventional system 65. Thus, the task-based interventional system 65 can be adapted to accommodate a variety of needs and circumstances.

b. Exemplary User Computing Entity

Figure 3:
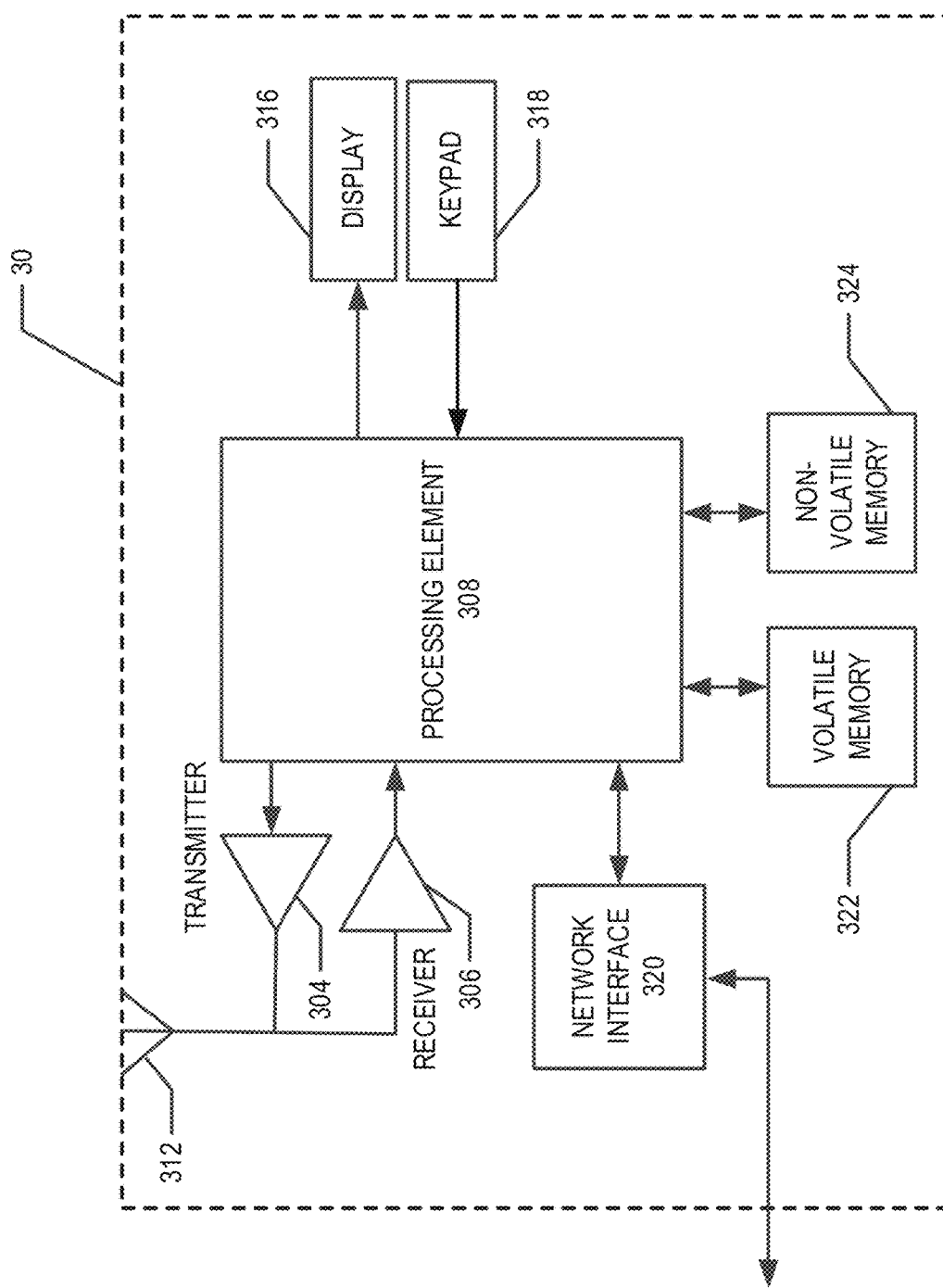
FIG. 3 is a schematic of a user computing entity in accordance with certain embodiments of the present invention.

FIG. 3 provides an illustrative schematic representative of user computing entity 30 that can be used in conjunction with embodiments of the present invention. As will be recognized, the user computing entity 30 may be operated by an agent and include components and features similar to those described in conjunction with the task-based interventional system 65. Further, as shown in FIG. 3, the user computing entity 30 may include additional components and features. For example, the user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a task-based interventional system 65, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing entity 30 may operate in accordance with multiple wireless communication standards and protocols, such as GPRS, UMTS, CDMA2000, 1×RTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data/data may be determined by triangulating the position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, user interface, dashboard, webpage, and/or similar words used herein interchangeably executing on and/or accessible via the user computing entity 30 to cause display or audible presentation of information/data and for user interaction therewith via one or more user input interfaces. The user output interface may be updated dynamically from communication with the task-based interventional system 65. The user input interface can comprise any of a number of devices allowing the user computing entity 30 to receive information/data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, the networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

III. EXEMPLARY SYSTEM OPERATION

Details regarding various embodiments are described with respect to FIGS. 4-9 herein. As discussed herein, certain embodiments are configured to improve the effectiveness of patient and provider outreach activities by creating robust and sophisticated decision support methods executing via a task-based interventional system to optimize the stratification of gap in care opportunities and ensure provider and/or payer representatives are taking the next best action to encourage completion of a targeted action item to close the gap in care and to extend the use of existing HEDIS engines beyond only reporting numerators and denominators of various HEDIS measures by incorporating explanations of what measure compliance criteria were not met and specifically why.

a. Overview

Various embodiments are directed to systems and methods for generating one or more task data objects having an executable portion for identifying a relevant computing entity (e.g., user computing entity) and transmitting at least a portion of the task data object (e.g., data identifying an action item to be completed by one or more entities) to the identified relevant computing entity to cause generation of an alert at the relevant computing entity indicative of content of the task data object. In various embodiments, the described system may be configured to monitor claims data generated and/or stored within a claims data storage area and that are indicative of completed action items corresponding to particular individuals. Through access to the claims data, various embodiments are configured to determine whether a particular action item has been completed, for example, before or after generating a task item data object.

Specific configurations as discussed herein are configured for evaluation of Healthcare Effectiveness Data and Information Set (HEDIS) measures to identify gaps in care of a specific patient and to generate task data objects corresponding to gaps in care to facilitate closure thereof. Accordingly, various embodiments are configured to review patient data corresponding to a particular patient (e.g., identified for analysis via manual selection or automated selection) to identify relevant identifying data of the patient. The system may then retrieve claims data relevant to the patient from the claims data storage system based at least in part on the identifying data of the patient. The system reviews the claims data and determines one or more programs for which relevant HEDIS requirements are specified, and for which program data is stored. The system retrieves relevant program data and identifies specific gaps in care indicating HEDIS requirements that are not indicated as satisfied by the claims data, and the system identifies one or more action items sufficient to close the identified gaps in care for the patient.

The system is configured to review patient data, provider data (of relevant providers), payer data, and/or the like (including historical data and/or profile data) via rule-based and/or machine-learning models to generate a longitudinal view of an individual gap in care, for example, in the context of a contract's current performance, financial upside, the patient's propensity to engage, the patient's propensity to close a gap in care, communication channel effectiveness, among other predictive analytics which may drive more intelligent and sophisticated stratification of gap in care closure activities, thereby enabling the system to identify an optimal mechanism via which to facilitate closing of the identified gap in care. For example, the system determines a patient's likelihood of closing a particular gap in care, the patient's receptiveness to communications from various entities (e.g., a determination of how likely the patient is to complete a given action item based on how the needed action item is communicated to the patient), and/or the like to identify a relevant entity for communicating the action item to the patient and a relevant intervention for providing data indicative of the action item to the patient (e.g., the provider calling the patient; a payer representative calling the patient; the payer sending a mailing to the patient; the provider sending an email to the patient; and/or the like). The system of certain embodiments generates a task data object comprising data indicative of the needed action item for closing the gap in care, data identifying an intervention for providing data indicative of the needed action item to the patient, and data identifying an executable job for providing data to the relevant individual. The executable job may comprise an executable task for the described system for transmitting a notification to a relevant external computing entity (e.g., a user computing entity) associated with the identified relevant individual; an executable task for populating a workflow object within a workflow software system; and/or the like.

Because the system at least periodically monitors the claims data corresponding with the patient, the system is configured to determine if/when the gap in care is closed, as well as the actual action item taken by the patient to close the gap in care. Such data is then utilized by the described machine learning models for better predicting methodologies for closing future gaps in care.

1. Technical Problem

Historically systems have been incapable of consistently identifying optimal mechanisms through which to facilitate completion of action items by various individuals, particularly for facilitating closure of gaps in care identified through HEDIS measures relating to patient care. Systems have been incapable of providing sufficient information regarding the types of action items needed, and existing systems have been incapable of determining a best method through which to facilitate execution of the needed action items based at least in part on relevant historical data and/or profile data of the patient. Thus, existing systems rely on redundant and manual processes for estimating what action items are needed for particular patients and/or for estimating a particular methodology for contacting an individual (e.g., a patient) to prompt the completion of an action item.

2. Technical Solution

To provide consistency across a large data set in determining appropriate action items and for initiating tasks encompassing those action items through computer-executable jobs for providing data of relevant action items to external computing entities (e.g., user computing entities). The identification of appropriate executable jobs, as well as the identification of relevant external computing entities may be performed through a combination of rule-based and machine learning-based selection engines for identifying optimal task combinations for assembly of a task data object to facilitate completion of the needed action item.

The intelligence created on quality measures may help payers and providers focus on the highest value opportunities as well as on how HEDIS measures are being addressed, taking out guess work. A health plan can benefit by eliminating manual research as to why a patient has not closed a gap in care, optimizing patient and provider outreach through more robust stratification, and creating more comprehensive reporting by incorporating contract performance/predictive analytics, patient engagement/campaign execution tracking, and financial forecasting and modeling. Providers can benefit by using their time more productively by focusing on true patient gaps in care. Providers can also benefit with MACRA (Medicare Access and CHIP (Children's Health Insurance Program) Reauthorization Act) and MIPS (Merit-based Incentive Payment System) reporting which is also based on select HEDIS codes.

Using a variety of data inputs discussed herein, a task-based interventional system 65 processes through logic using predefined rules, Artificial Intelligence (AI) and Machine Learning (ML) to derive outputs indicative of one or more care scores and/or a next best action item (or a plurality of alternative or sequential next best action items) for closing a gap in care. Rule-based and/or machine learning based models are applied to layer in the logic needed to build an accurate care score to determine the next best action. The care score derived through intelligent measures helps payers and providers improve analytics and decisions on what actions to take to close gaps in care. The overall approach improves gap in care outcomes with improved predictability of cost to create a more accurate view of the patient for the payer and provider to provide the most appropriate care.

b. Data Stores

As mentioned above, a task-based interventional system 65 references data stored in a plurality of data stores as input for a plurality of rule-based and/or machine learning-based models to identify gaps in care, appropriate action items to satisfy the identified gaps in care, and for generating task data objects configured to initialize workflows to facilitate execution of action items.

As shown in FIG. 2B, patient data may be stored in a corresponding patient data store. The patient data may be stored as a plurality of patient profiles, each having corresponding individual data items and/or data objects indicative of data relevant to a particular patient. For example, a patient profile may comprise identifying data of a patient, such as patient name, one or more unique identifiers (e.g., assigned by the task-based interventional system 65 and/or another system), a patient date of birth, a patient gender, patient weight, patient height, patient skin color, patient eye color, patient hair color, and/or the like. The patient profile may comprise data usable for correlating data in other data storage areas, such as data within a claims data store with individual patients. Moreover, the patient data may comprise communication data corresponding with the patient, such as an email address, a phone number, a mailing address, a residential address, a social media handle, an account identifier associated with a healthcare-related notification system, and/or the like.

Moreover, the patient data may additionally comprise historical data, such as data indicating previous interventions provided to the patient (alternatively, such historical data may be stored as claims data, with appropriate identifiers utilized for associating the patient profile with relevant historical claims data). Such historical data may be defined as a plurality of intervention data objects each comprising data identifying a time stamp of a corresponding intervention, a type of intervention (e.g., a mailing, an in-person visit, a telephone call, an email message, and/or the like), the content of the intervention (e.g., a textual summary of information provided to the patient during the intervention; an embedded or linked data object of the intervention provided to the patient (e.g., a copy, a recording, and/or the like), an entity providing the intervention (e.g., a payer, a provider, and/or the like), and/or the like. The historical data embodied as the intervention data objects may additionally comprise data indicating whether the historical intervention was successful. Such data may be reflected as a summary indicating whether the patient responded positively or negatively to the intervention, the time/date at which the patient responded, and/or the like. In other embodiments, such data may be reflected as a data link (e.g., an inter-data store reference) to a particular claim data object indicating success of an intervention (e.g., indicating the patient completed the action item referenced during the intervention).

As also shown in FIG. 2B, provider data may additionally be stored within a provider data store. Like the patient data, the provider data may be stored within a plurality of provider profiles each having corresponding individual data items and/or data objects indicative of data relevant to a particular provider. For example, a provider profile may comprise identifying data of a provider, such as a provider name, one or more unique identifiers (e.g., licensing identification numbers, unique identifiers assigned by the task-based interventional system 65 and/or another system), a provider group affiliation (e.g., a provider hospital affiliation), a provider type (e.g., physical therapist, optometrist, cardiologist, internist, nurse practitioner, and/or the like, which may be identified by name, by a reference identifier, and/or the like), and/or the like. The provider profile may comprise data usable for correlating data in other data storage areas, such as data within a claims data store with individual providers. Moreover, the provider data may comprise communication data corresponding with the provider, such as an email address, a phone number, a mailing address, a business address, an account identifier associated with a workflow system utilized by the provider and/or the providers' group affiliation, and/or the like.

In certain embodiments, the provider data additionally comprises historical data indicative of one or more interventions provided by the providers (or the historical intervention data may be stored within the claims data storage area with appropriate unique identifiers for linking the claims data with a relevant provider). Such provider-centric intervention data objects may each comprise a time stamp indicating when an intervention was conducted, a type of intervention conducted, content of the intervention (e.g., a summary, embedded or linked objects, and/or the like). Moreover, the provider-centric intervention may comprise data indicating a success rate associated with an intervention. For example, the success data may be reflected as a summary of whether the intervention was successful, a link to claim data indicating that an action item was completed based on the intervention, and/or the like.

Moreover, payer data may be stored within one or more payer profiles of a payer data storage area 213. The payer profiles may comprise identifying data, such as a payer name, one or more payer representatives (and/or one or more unique identifiers associated with each of the one or more payer representatives), and/or the like. The payer profiles may comprise data usable for correlating data in other data storage areas, such as data within a claims data store with a corresponding payer, payer representative, and/or the like. Moreover, the payer profiles may additionally comprise communication data usable for corresponding with a payer and/or payer representative (e.g., correspondence between a payer and member, correspondence between a payer and a task-based intervention system 65, and/or the like), such as an email address, a phone number, a mailing address, a web address, and/or the like.

In certain embodiments, the payer data additionally comprises historical data indicative of one or more interventions provided by the payers (and/or payer representatives). Such payer-centric intervention data objects may each comprise a time stamp indicating when an intervention was conducted, a type of intervention conducted, content of the intervention (e.g., a summary, embedded or linked objects, and/or the like). Moreover, the payer-centric intervention may comprise data indicating a success rate associated with an intervention. For example, the success data may be reflected as a summary of whether the intervention was successful, a link to claim data indicating that an action item was completed based on the intervention, and/or the like.

As additionally illustrated in FIG. 2B, claims data may be stored within a claims data store 214. The claims data may be embodied as a plurality of claims data objects generated by the task-based interventional system 65 and/or provided for storage within the claims data store by an external system (e.g., a healthcare claims generation system; a pharmacy claim generation system; a lab claim generation system; and/or the like). Accordingly, the claims data may be representative of healthcare related claims generated during the course of treating one or more patients. Thus, each claim data object may be embodied as a collection of data relating to a discrete event, transaction, prescription, and/or the like. Each claim data object may comprise identifying data of the claim, such as a timestamp associated with the claim, a patient associated with the claim, a provider associated with the claim, a payer associated with the claim, a cost associated with the claim (e.g., a cost of a procedure, a cost of an episode, and/or the like), and/or the like. The claim may additionally comprise data identifying one or more codes associated with the claim, such as procedure codes, prescription codes, diagnosis codes, and/or the like. In certain embodiments, the claims may additionally comprise data indicative of one or more programs for which the claim data was generated.

The illustration of FIG. 2B additionally indicates that program data may be stored within a program data store. The program data may be indicative of various programs to which a patient, a payer, or a provider may subscribe, and which may be dependent on a particular patient satisfying particular criteria. Programs may define eligibility criteria for receiving certain healthcare related payments, for receiving healthcare related services, and/or the like. It should be understood that programs may be utilized for defining criteria for other benefits in other healthcare related contexts, and may be utilized for defining other criteria/requirements for promotions, discounts, membership, subscriptions, and/or the like in other non-healthcare related contexts, as just a few non-limiting examples. Accordingly, programs may have corresponding program profiles stored within the program data store. Each program profile may be embodied as a data object comprising identifying data of the program, eligibility criteria for the program; compliance criteria for the program; associated time frames for eligibility and/or compliance with the program (e.g., time frames establishing maximum and/or minimum amounts of time during which a patient can satisfy all of the requirements for eligibility; maximum and/or minimum amounts of time during which a patient can satisfy compliance requirements of the program; and/or the like); costs associated with the program (e.g., cost per intervention, cost per member, and/or the like); and/or the like. As a part of establishing various requirements for a program, the program profile may identify one or more claim data aspects that satisfy various requirements (e.g., diagnosis codes, procedure codes, pharmacy codes, provider types, patient identifying data, and/or the like), as well as textual descriptions of the requirements that may be utilized to populate a graphical user interface indicating various requirements that have not been satisfied for a particular program.

It should be understood that the memory media 206 (e.g., data store) may additionally store various executable program attributes of certain embodiments, which may enable generation of various software-related outputs in accordance with certain embodiments.

c. HEDIS Engine

A HEDIS engine provided in accordance with embodiments discussed herein is specifically configured for providing granular information to users regarding requirements of various programs attributable to particular patients, and for identifying discrete gaps in care corresponding to those programs, thereby enabling a determination of appropriate action items for closing those identified gaps in care.

Figure 4:
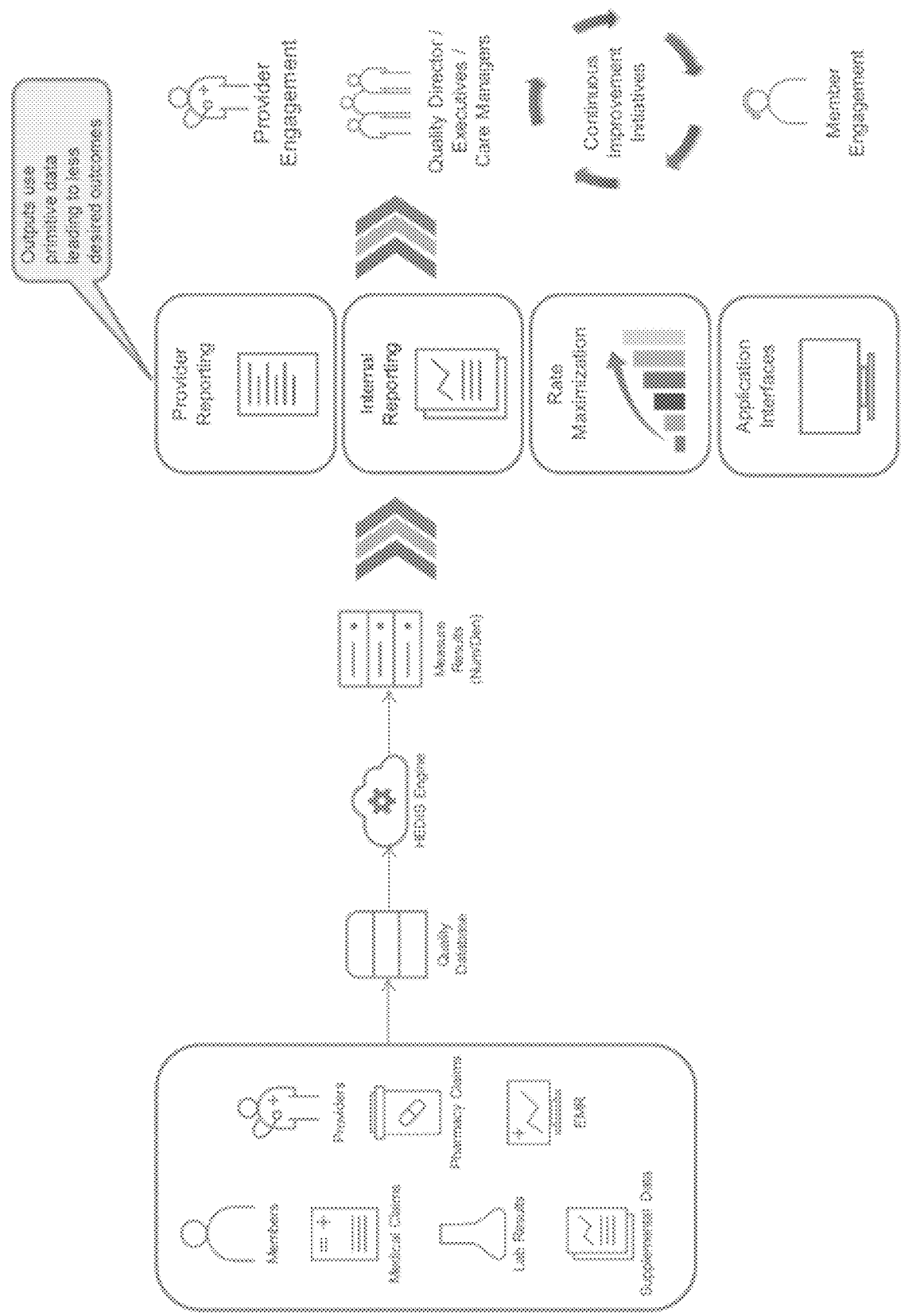
FIG. 4 is a flow diagram illustrating operation of a HEDIS engine according to certain embodiments.

HEDIS engines are certified for each measure by NCQA (National Committee for Quality Assurance) using medical claims, pharmacy claims, lab results, patient data, and various supplemental data. FIG. 4 illustrates a flow diagram corresponding to operation of an existing HEDIS engine, which is merely configured for providing binary data indicative of whether a particular patient is "eligible or "not-eligible" and whether the patient is "compliant" or "not-compliant" based on requirements of various programs. Such configurations comply with NCQA requirements, which does not require a HEDIS engine to provide specifics on why or how a patient's claim closed a HEDIS measure or how a member was placed into a numerator or denominator of a particular measure. Thus, existing HEDIS engines intake claims data provided from various sources, and simply output primitive data reports indicating eligibility and/or compliance with various programs. However, providers, patients, and/or payers are required to manually determine the underlying reasons why a particular patient may be ineligible or non-compliant with requirements of a particular program. This lack of transparency and information leads to increased costs associated with providers and/or payers duplicating efforts to determine whether particular procedures have been previously completed, to determine whether particular lab tests have been previously completed, to determine characteristics of previous claims, and/or the like.

Implementing a process to capture reasons a patient's claim created or did not create a denominator and numerator entry of a particular measure (or other program), and additionally providing data outputs indicating why or why not would help payers and providers understand why the specific rules were not met. The insight created by such an engine may provide input for decision sciences to determine optimal approaches for capturing the proper information required or to determine if all possible options have been exhausted. Relying on existing HEDIS engine architecture, significant amounts of time, resource and capital are placed into following up with providers or patients by providers and payers on why a patient is not compliant with a HEDIS measure. Data research, phone calls, faxes, emails, and resources staffed within provider settings and payers to focus specifically on these activities results in significant healthcare spend.

Via more granular data providing approaches, patient and provider engagement approaches and incentives would be better informed. As just one non-limiting example of a particular program, the Comprehensive Diabetes Care Eye Exam HEDIS measure requires a provider specialty of either optometrist or ophthalmologist. If a claim is not tagged with the correct specialty, a gap in care remains open, even if the patient took the appropriate steps to visit a care provider. While the claim is paid, the HEDIS measure is not considered compliant and therefore CMS does not accept that the payer and provider are providing the best quality treatment based on the measurement logic although they may have missed a procedure code and/or mis-coded a procedure while not understanding the parameters of the specific HEDIS numerator and denominator rules. Informing the provider and payer of the coding and what it means will help coach both on if the claim can be re-coded to identify the proper information for CMS.

Current processes also do not help inform payers or providers if a patient has actually been seen within timeframes of the HEDIS rules or if they are or are not eligible for a specific measure based on time with plan or other criteria. Additional outreach or unnecessary requests to follow-up may occur, thereby adding cost and/or interruption to providers and patients when the adjustments could be made knowing specifically what is needed.

Figure 5:
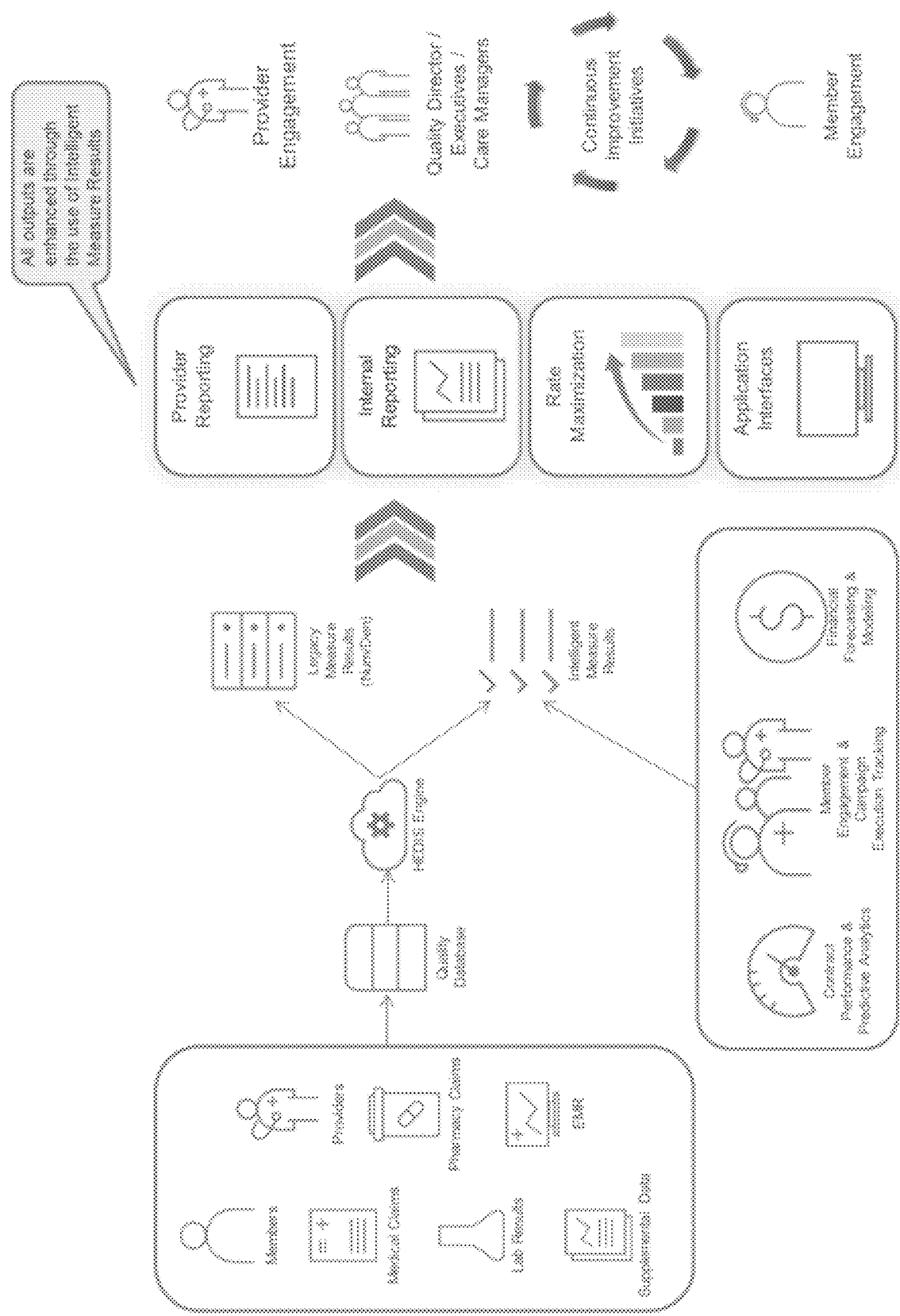
FIG. 5 is a flow diagram illustrating operation of a HEDIS engine according to a plurality of embodiments.

Thus, HEDIS engines provided in accordance with embodiments as discussed herein provide increased granularity of information, thereby facilitating the identification of particular action items for closing gaps in care associated with particular programs. As shown in the illustration of FIG. 5, a HEDIS engine configured in accordance with certain embodiments intakes claims data provided from various sources via a quality database (e.g., a claims data store). The HEDIS engine is configured to output a plurality of data outputs, including binary eligibility and compliance data (e.g., indicating whether a member is eligible and/or compliant with various programs), as well as granular data indicating which requirements have (or have not) been satisfied for eligibility and/or compliance with a particular program. The granular output of the HEDIS engine may be supplemented with various action item analyses, as discussed in greater detail herein, for distinctly identifying optimal action items for closing identified gaps in care, as well as for identifying most-appropriate intervention strategies for maximizing a likelihood of completion of the identified action items. The resulting output may be further supplemented with executable job data objects that are configured to automatically initialize the identified intervention strategy by initializing computer-specific aspects of the intervention strategy, such as by generating data objects for execution by appropriate workflow software systems, for generating computer-based alerts to be transmitted to various actors (e.g., providers, payer representatives, and/or the like), and/or the like to begin the interventional strategy, such as to provide appropriate patient engagement to encourage completion of the identified action items.

Accordingly, HEDIS engines provided in accordance with various embodiments (e.g., as a part of a task-based interventional system 65) facilitate the closure of various gaps in care without unnecessary outreach to patients to confirm the completion of various action items. Moreover, the HEDIS engine provided in accordance with certain embodiments provides sufficiently granular data regarding outstanding gaps in care so as to enable detailed cost-benefit analysis of various interventional strategies that would result in the closure of the gap in care if those interventional strategies are successful in encouraging completion of a particular action item, thereby further reducing unnecessary spending toward cost-ineffective interventional strategies, as well as for minimizing unnecessary spending for interventional strategies for gaps in care that a patient is likely to self-close, without any intervention. Accordingly, the overall number of gaps in care may be reduced (thereby improving overall health outcomes for patients), as well as the amount of payer and provider costs accrued during procedures for attempting to close gaps in care.

For example, contract performance data may be received and analyzed, and may include real-time compliance tracking for each contract against predicted measure thresholds. This contract performance data may be provided, for example, as a part of the payer data stored within the payer data storage area, thereby enabling the contract performance data to be input into the intelligence engine to enable insights into which contracts and corresponding gaps in care will lead to the greatest improvement in compliance rates and subsequently improved HEDIS/Stars ratings. Moreover, financial forecasting and modeling data may provide line of sight to contract level revenue opportunity to be used to prioritize gap in care closure activities. Predictive analytics (e.g., using machine learning models, using rule-based models) can be used for predictive HEDIS measure thresholds, competitor performance, patient and provider behavior, channel effectiveness, and/or the like. For example, the machine-learning based modeling processes may perform machine-learning based analysis to identify likely HEDIS measure thresholds (e.g., based on received data indicative of various percentile levels (e.g., a $25^{th}$ percentile, a $50^{th}$ percentile, a $75^{th}$ percentile, and/or the like, as well as rules indicating percentile-based cut-points) together with confidence scores by comparing a plurality of characteristics against historical data, such as by translating the plurality of characteristics into representative vectors that may be effectively compared against vector-based representations of other historical data, wherein those vector-based representations of other historical data is associated with corresponding HEDIS measure thresholds and/or may be associated with adjustment factors for adjusting a HEDIS measure threshold by adjusting a HEDIS measure threshold by an adjustment amount corresponding to a particular historical data vector deemed relevant to a particular claim. Propensity to close data provides insights into patient gap closure behavior and can be used to prioritize patient and provider outreach. Propensity to engage data provides insight into the likelihood that a patient will actively engage in provider or health plan outreach and take action.

FIGS. 6A-6B provide example outputs of HEDIS engines according to various embodiments. Specifically, FIG. 6A provides an example binary-style output for patients indicating eligibility and compliance with requirements of an example "Comprehensive Diabetes Care—Eye Exam Measure" program. Although this data is useful for providing a quick view of the status of patients regarding this particular program, such data does not provide any indication regarding why a particular patient is ineligible or non-compliant with particular requirements of the program. This information may be provided by HEDIS engines in accordance with certain embodiments together with more granular data outputs such as those illustrated in FIG. 6B. FIG. 6B provides an example graphical user interface illustrating specific eligibility criteria and compliance criteria for the Comprehensive Diabetes Care—Eye Exam Measure program for those patients also illustrated in FIG. 6A. As shown, the individual requirements for eligibility and compliance are provided together with a graphical indication showing whether the particular requirement has been satisfied, has not been satisfied, or has not been evaluated.

In the first example, John Doe is listed as "Not Eligible" for the Comprehensive Diabetes Care Eye Exam (CDCEYE) Measure in the display of FIG. 6A, but no further information is provided as to why he is not eligible. Using HEDIS engines providing only the simple output of FIG. 6A, data analysts would need to perform research and analysis on the data to determine the cause. In accordance with embodiments as discussed herein providing output in accordance with the illustration of FIG. 6B, the output indicates that John Doe did not meet the continuous enrollment eligibility criteria and also has an applicable exclusion (e.g. Hospice).

In the second example, Sally Smith is listed as "Eligible, Not Compliant" for the CDCEYE Measure in the display of FIG. 6A, but no further information is provided as to why she is not compliant. Based on this information, a payer may commence provider and patient outreach activities to encourage the patient to have an eye exam completed, even though evidence is provided that an eye exam has already been completed. This may be wasted effort and could lead to provider/patient abrasion since we have evidence that the patient already had an eye exam. In accordance with embodiments as discussed herein providing output in accordance with the illustration of FIG. 6B, the display indicates that Sally has had an eye exam, but the specialty listed on the claim is not optometrist or ophthalmologist and therefore does not meet NCQA's criteria to close a gap. With this additional intelligence, the payer may choose to look into their specialty mapping process or other internal data process first before engaging the provider/patient.

In the third example, Joe Blow is listed as "Eligible, Compliant" for the CDCEYE Measure in the display of FIG. 6A, but no further information is provided regarding eligibility and/or compliance requirements. By contrast, embodiments as discussed herein providing output in accordance with the illustration of FIG. 6B provides data regarding all requirements of the program that may be relayed to Joe Blow, if necessary. While this use case may not result in a change in outreach, it does provide immediate insight into why a patient is eligible and compliant for a measure in the event a question is raised about this particular member and measure.

Accordingly, users viewing the graphical user interface are provided with detailed information regarding why a particular patient has not satisfied all relevant requirements for a particular program. Moreover, although not shown in the figures, each requirement may be embodied as a hyperlink in certain embodiments, such that selection of a corresponding hyperlink provides a user with a graphical user interface providing additional detail about the requirement, such as action items and/or claims that are deemed sufficient to satisfy applicable requirements.

d. Action Item Analysis

Figure 7A:
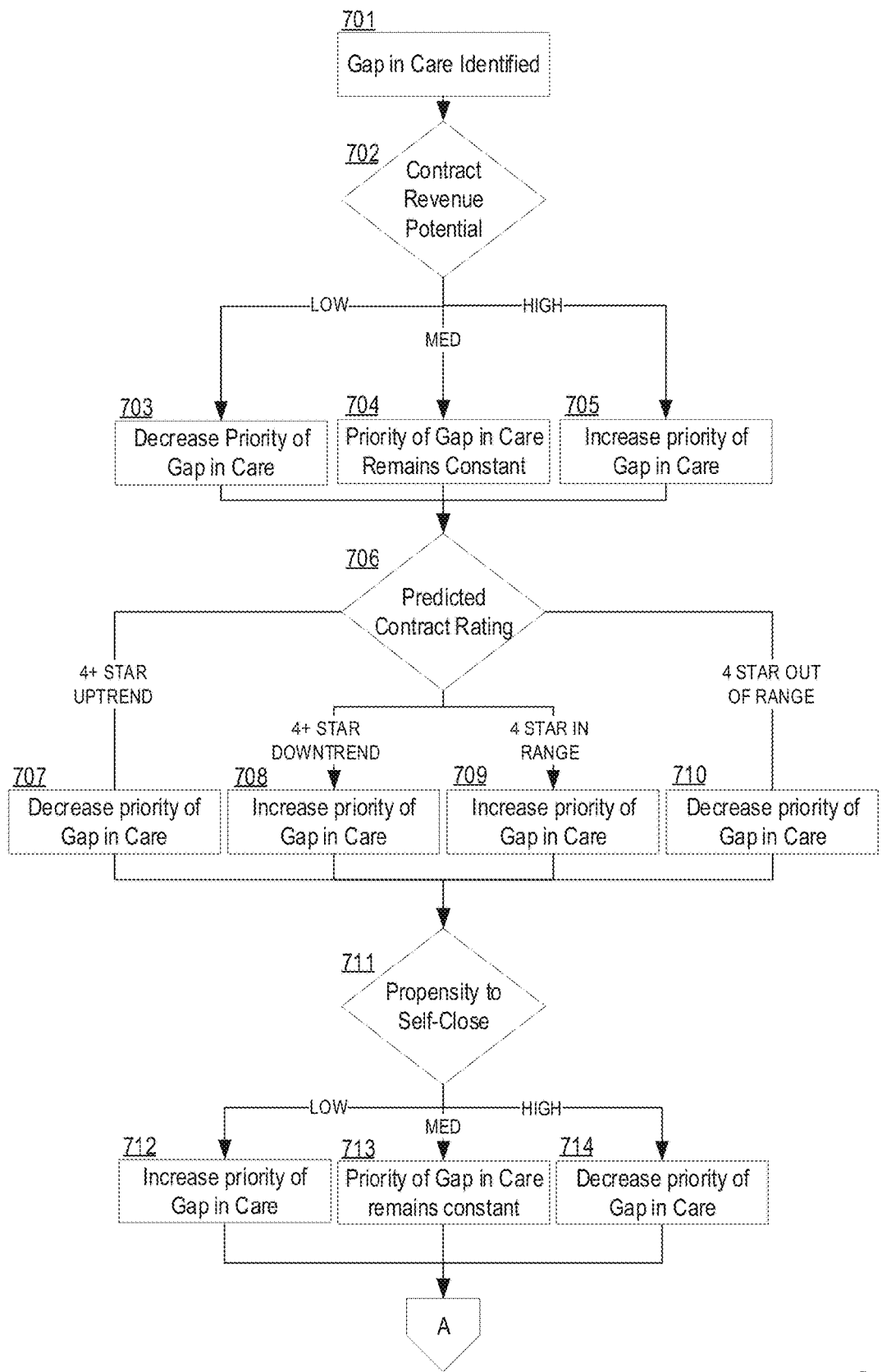
FIGS. 7A-7C collectively illustrates a flowchart demonstrating steps according to certain embodiments.
Figure 7B:
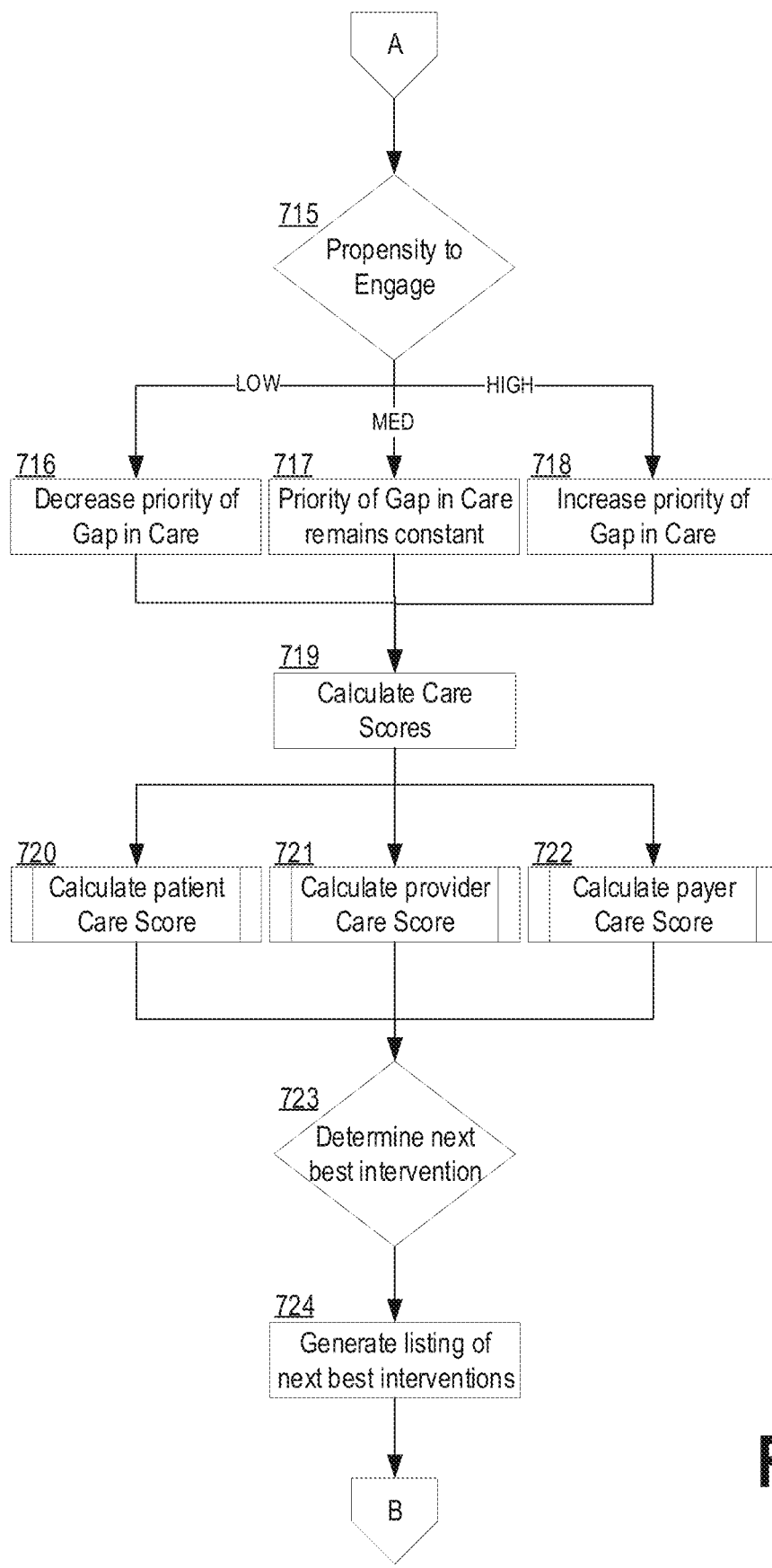
Figure 7C:
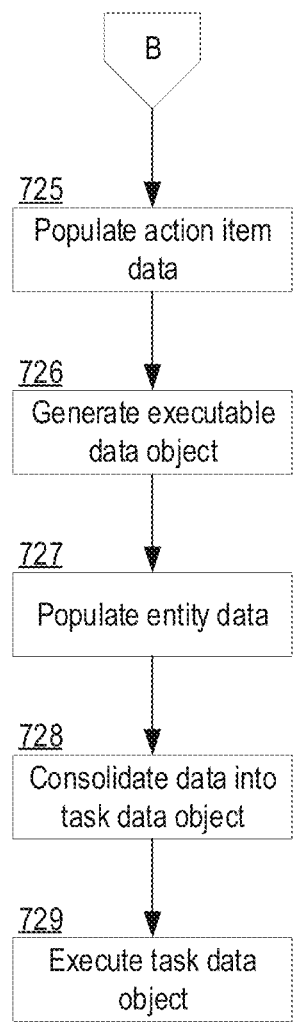

The flowchart of FIGS. 7A-7C illustrates processes associated with analyzing various action items associated with an identified gap in care to determine an optimal action item (also referred to herein as a next best action) to be performed to close the gap in care. As illustrated therein, upon identifying a gap in care (as shown at Block 701), for example, via the HEDIS engine discussed above (e.g., by identifying particular eligibility and/or compliance requirements that have not been satisfied for a particular patient's use of a specified program, the task-based interventional system 65 as discussed herein is configured to begin analysis of various action items to assemble such action items into a task data object with executable portions configured to cause one or more computing entities to execute various software processes (e.g., generation of workflow software data items that cause initiation of a particular action item; generation of a notification to be provided to a user computing entity 30), and/or the like.

As a part of the action item analysis, action items and/or the corresponding gap in care may be assigned a care score indicative of a priority of addressing the gap in care. The care score may be assigned via a rule-based analysis (e.g., by increasing or decreasing a care score based on the results of various analytical steps), an artificial intelligence-based analysis (e.g., determining an appropriate care score by assigning weights established via machine-learning models (e.g., time-series based anomaly detection, regression modelling (e.g., Bayesian modelling, Linear modelling, Neural Network modelling, and/or the like), clustering, and/or the like), which may assign weights based on comparisons with historical data that may be performed within a vector-based domain), and/or a combination of rule-based and artificial intelligence-based models. As just one example, each gap in care identified via the task-based interventional system 65 may be assigned an initial care score (e.g., a care score of 1, however, other scoring methodologies/reference points may be utilized in other embodiments) that may be increased or decreased based on the results of various analyses as discussed herein.

Analytical processes for determining a priority of a gap in care (and/or one or more action items identified as relevant for addressing a gap in care) may encompass processes for analyzing contract revenue potential associated with closing a particular patient's gap in care; predicting contract ratings resulting from closure of a gap in care; determining a patient's propensity to self-close a gap in care without intervention; determining a patient's propensity to engage various intervention types; and/or the like.

Block 702 illustrates analytical steps for determining contract revenue potential associated with closing a gap in care. The contract revenue potential may be associated with a particular payer and/or provider, and may be indicative of one or more payments that may be received by the payer and/or provider by satisfying certain care-based criteria associated with a payment, such as maintaining less than a maximum threshold of open gaps in care (e.g., overall, relating to a particular program, and/or the like), satisfying particular HEDIS-star rating, and/or the like. Data indicative of such contract revenue potential may be stored within the payer data store and/or the program data store in certain embodiments.

In accordance with certain embodiments, the task-based interventional system 65 determines gap in care quality thresholds corresponding with particular programs (e.g., a program prompting a gap in care being analyzed). For example, the task-based interventional system 65 defines and/or receives STAR rating thresholds by program for satisfying requirements of particular programs. As a part of this analysis, the task-based interventional system 65 may receive, as input, data from an external system indicative of CMS STARs quality thresholds by market and quality measure. Such STAR ratings thresholds may be utilized to determine the aggregate effect of closing a gap in care of a particular patient relative to any quality thresholds deemed relevant based at least in part on the STAR rating thresholds (e.g., determining whether the closure of a particular gap in care is likely to contribute to an aggregate improvement in a payer's ability to satisfy STAR rating thresholds for a particular program. It should be understood that such configurations are provided as mere examples, and other ratings, reviews, and/or other systems may be utilized in certain embodiments. Moreover, it should be understood that a particular program may have uniform requirements for eligibility and compliance for all patients, although in certain embodiments, requirements may be different for different subsets of patients, such as patients associated with different health plans. Thus, when identifying gaps in care and required action items for addressing those gaps in care, the task-based interventional system 65 is configured to identify appropriate requirements for addressing gaps in care by retrieving data indicative of requirements that are relevant to a particular patient (e.g., by identifying a health plan associated with the patient based on data within the patient's profile and retrieving relevant program requirements from a program profile based on the associated health plan).

Upon determining gap in care quality thresholds, the task-based interventional system 65 may determine a financial impact of closing a particular gap in care. The financial impact may be determined with relevance to the patient, one or more relevant providers, one or more relevant payers, and/or the like. Moreover, the financial impact may be determined on a micro-scale, with individual relevance to the care of the single patient, or on a macro-scale based on aggregated information corresponding to a plurality of patients. For example, the task-based interventional system 65 may determine STAR level payments by regional level and/or STAR measure. The task-based interventional system 65 may additionally determine risk adjustment HEDIS measure payments and/or other payment methods based on quality measures at an individual patient level. The task-based interventional system 65 may rely on inputs of CMS STAR payment thresholds by market and/or quality measure; and/or CMS risk adjustment payment models, which may be provided by an external system in accordance with certain embodiments.

The task-based interventional system 65 may additionally be configured to determine costs associated with outreach and/or engagement with various parties (e.g., costs associated with the payer reaching out to the patient and/or a relevant provider; costs associated with the provider reaching out to the patient; and/or the like). These costs may be determined for various available intervention types (e.g., telephonic, mailer, email, text message, in-person, and/or the like), and may be determined at least in part based on inputs received by the task-based interventional system 65 indicative of intervention program costs to perform various outreach types.

Thus, the task-based interventional system 65 may utilize various data generated as discussed above to determine an overall contract revenue potential associated with closing a particular patient's gap in care by determining costs associated with outreach (having a negative impact on contract potential) as well as potential cost savings and/or revenue increases associated with closing the gap in care (e.g., considering payments that may be provided to a payer and/or a provider for satisfying aggregate care standards across a plurality of patients), as well as determining how closing a gap in care would impact those potential revenue payments. As indicated at Blocks 703-705, the care score may be decreased for low contract revenue potential (e.g., contract revenue potential falling below a defined threshold), the care score may remain constant for medium contract revenue potential (e.g., contract revenue potential falling between defined threshold amounts), or the care score may be increased for high contract revenue potential (e.g., contract revenue potential exceeding a defined threshold).

The analysis of a gap in care and/or action item may continue as indicated at Block 706, by predicting a contract rating associated with closing a gap in care. For example, the task-based interventional system 65 may initial determine gap in care rating thresholds, such as predictions based on competitor data and/or cut points to achieve certain STAR ratings (e.g., 4 star or 5 star). Such data may additionally be predicted utilizing data associated with other patients (e.g., anonymized data associated with other patients) provided to a machine learning model (e.g., a regression model (e.g., Bayesian, Linear, Neural Network, and/or the like) a clustering model, and/or the like) for determining predicted STAR ratings.

For example, the machine-learning based modeling processes may perform machine-learning based analysis to identify likely STAR ratings together with confidence scores by comparing a plurality of characteristics against historical data, such as by translating the plurality of characteristics into representative vectors that may be effectively compared against vector-based representations of other historical data, wherein those vector-based representations of other historical data is associated with corresponding STAR ratings.

Such data may additionally be generated based at least in part on the above-mentioned input indicative of CMS STAR quality thresholds by market and/or quality measure. Utilizing the determined gap in care rating thresholds, the task-based interventional system 65 of certain embodiments determines an ability to achieve a particular rating (e.g., a likelihood of exceeding a minimum rating threshold), at least in part, by evaluating historical data associated with the patient and/or the provider to determine historical performance to-date and to apply artificial intelligence models to predict the ability to achieve a desired STAR rating level for various measures. As a part of evaluating historical data, various embodiments determine a year-to-date and/or other historical determination of closing gaps in care to determine a likelihood of closing sufficient gaps in care for reaching a threshold level to reach a particular HEDIS/Star rating. In various embodiments, the output of such a determination of a likelihood of satisfying a particular threshold/rating may be a trending indicator (e.g., trending upward, trending downward, no trend) or a score that may be indicative of a trend or an ability to achieve a desired rating level.

Moreover, as a part of predicting a contract rating resulting from a closure of a gap in care, the task-based interventional system 65 calculates a weighted risk probability for the patient for example, via artificial intelligence modelling for evaluating historical data associated with the patient, relevant provider(s), and/or payer to determine leading indicators and/or a probability of satisfying criteria necessary for closing a gap in care. Such analysis may utilize a machine-learning based model utilizing data indicative of perennially difficult-to-close gaps in care to determine a best-chance area of focusing further analysis. For example, the task-based interventional system 65 executes historical trend analysis to assess provider performance, considering historical data corresponding with the provider to determine a provider's performance in closing various gaps in care. Moreover, the task-based interventional system 65 is configured to execute one or more machine learning based models (e.g., time series anomaly detection models, regression models (e.g., Bayesian regression models, linear regression models, neural network regression models), clustering models, and/or the like) to identify highest performing patients and/or providers (e.g., determined based at least in part on patient and/or provider scores assigned based on various characteristics of historical data corresponding with the patients or providers, such as a number of open gaps in care, percentage of gaps in care that remain open, and/or the like). Moreover, the task-based interventional system 65 may execute advanced analytics to determine efficacy in a patient's region (e.g., prevalence of particular gaps in care in a geographical region associated with the patient as well as prevalence of closures in the gaps in care in the identified geographical region associated with the patient), to determine efficacy in the patient's plan (e.g., prevalence of particular gaps in care in a particular plan in which the patient is subscribed as well as prevalence of closures in the gaps in care in the identified plan associated with the patient), efficacy given a patient's demographics (e.g., prevalence of particular gaps in care within a particular demographic group as well as prevalence of closing the particular gap in care within the particular demographic group), efficacy of patients having conditions analogous to the patient (e.g., prevalence of particular gaps in care in patients having conditions analogous to the patient as well as prevalence of closing those particular gaps in care within the grouping of patients identified as having conditions analogous to the patient), efficacy of patients having analogous social determinants of health factors (e.g., prevalence of particular gaps in care in patients having social determinant of health factors analogous to the patient as well as prevalence of closing those particular gaps in care within the grouping of patients identified as having social determinants of health analogous to the patient). Such modeling may utilize data inputs such as historical provider data, historical payer HEDIS data, patient-specific data, and/or the like.

The task-based interventional system 65 may utilize a machine learning model trained to generate a weighted risk probability (e.g., a non-linear risk probability) for a patient based at least in part on the output of the various analyses discussed above. Such analysis may be utilized to determine an overall likelihood of reaching a target program threshold (e.g., a sufficient percentage of patients for closing respective gaps in care). Based at least in part on this weighted risk probability for the patient, the task-based interventional system 65 may determine a predicted contract rating, which is indicative of a likelihood of closing the gap in care, as well as the likely impact the predicted gap closure (or predicted failure to close the gap) may have on a predicted contract rating (e.g., corresponding to a payer). As indicated at Blocks 707-710, the care score may be increased or decreased based at least in part on a current contract rating as well as a trend (e.g., an indication of whether the gap in care is likely to be closed and/or to impact the overall contract rating via an identified trend).

As indicated at Block 711, the task-based interventional system 65 may additionally determine a particular patient's propensity to close gaps in care without any intervention provided by the payer or provider. A high propensity of the patient to self-close a gap in care may be indicative that the cost of intervention is likely unwarranted without a specific reason why the patient's typical propensity to self-close gaps in care would be unlikely to address a particular gap in care identified as currently relevant to the patient. A determination of a patient's propensity to self-close gaps in care may be performed at least in part by evaluating historical data associated with the patient to determine the patient's historical probability of self-closing gaps in care. Such an analysis may be performed at least in part via an artificial intelligence model evaluating historical data indicative of HEDIS gaps in care associated with a patient, including data indicative of action items necessary to close such gaps in care (e.g., physician visits, patient health plan updates, data updates, and/or the like), as well as actions typically taken by the patient in various historical circumstances. Such data may indicate whether a patient is proactive in identifying needed action items and performing such action items, whether the patient passively schedules regular physician visits which are often sufficient to close various gaps in care (or initialize a process that results in a closure of a gap in care). Based on the evaluated historical data associated with the patient, the task-based interventional system 65 is configured to generate a weighted risk probability indicative of whether the patient is likely to self-close a particular identified gap in care. The weighted risk probability may be determined at least in part by evaluating historical data (e.g., associated with the patient, payer, and/or provider) against recent historical data (e.g., having a time stamp falling within a defined time period of the current time) to determine a probability of an individual patient closing a gap in care, as well an evaluation of any data indicating factors that may reduce a patient's likelihood of closing a particular gap in care. Such models may execute via input such as historical data associated with patients, providers, and/or payers, social determinants of health data (e.g., which may be reflected within patient profiles), and/or other input data indicative of real or perceived barriers to care, such as data regarding regional environmental impacts, familial environmental impacts, weather-related data, data regarding widespread disasters, epidemics, pandemics, and/or the like, or other data that may be provided to the task-based interventional system 65 as input for machine-learning based models. Such input may be provided, for example, in a vector-based domain to enable determinations of relative similarities between current claims data and data reflected within the data inputs of the machine-learning models.

As indicated in Blocks 712-714, the task-based interventional system 65 may increase or decrease the care score associated with a gap in care and/or a particular action item based at least in part on a patient's propensity to self-close gaps in care. For example, upon determining that the patient has a low propensity to self-close gaps in care, the care score may be increased, indicating a higher priority of intervening with the gap in care (e.g., a determination that an intervention may be necessary to close the gap in care). Upon determining that the patient has a high propensity to self-close gaps in care, the care score may be decreased, indicating a lower priority of intervening with the gap in care (e.g., a determination that an intervention may be unnecessary to close a gap in care). If a patient's propensity to close gaps in care is determined to be moderate, the care score may remain unchanged. Determinations of whether a patient has a high, moderate, or low propensity of closing gaps in care (and/or the specific gap in care of relevance) may be determined based on a generate score indictive of the propensity of a patient to close a gap in care. A score below a defined threshold may be indicated as a low propensity to close a gap in care; a score falling between high and low thresholds may be indicated as a moderate propensity to close a gap in care; and a score exceeding a high threshold may be indicated as a high propensity to close a gap in care.

With reference to Block 715 of FIG. 7A, the task-based interventional system 65 is configured to determine a patient's propensity to engage with intervention strategies, such as to provide an indication of whether a patient is likely to be receptive to various interventional strategies to suggest that a patient take a particular action to close a gap in care. To determine the patient's propensity to engage, certain embodiments of the task-based interventional system 65 are configured to retrieve historical data (e.g., patient historical data) indicating the patient's receptiveness to previous outreach activities. Such historical data may be manually populated database entries (e.g., indicating whether a patient responded to a particular outreach activity) or automatically populated database entries (e.g., indicating whether a particular patient clicked on a link of an electronically-provided outreach activity, such as an email; indicating whether the particular patient answered a telephonic call placed to the patient; and/or the like). Based at least in part on the historical data indicative of successful patient outreach activities, the task-based interventional system 65 is configured to identify optimal engagement/outreach approaches for the patient. Determining optimal engagement/outreach approaches may be performed via an artificial intelligence model defining a value of each outreach/engagement approach for the patient that is likely to influence the closure of a particular gap in care. Models may be intelligently selected for determining optimal outreach/engagement activities for individual patients, with the results of models based at least in part on historical data of certain patients being applicable for generating models appropriate for identifying optimal outreach/engagement activities for other patients. Accordingly, in certain embodiments, determining an optimal engagement/outreach approach for a particular patient comprises identifying an appropriate model for use in identifying optimal engagement/outreach approaches based on the patient-specific historical data. Identification of relevant models may be based at least in part on determined similarities between patient characteristics identified within respective patient profiles. Determinations of similarities between patients may be performed while maintaining anonymity, at least in part by performing analysis of patient characteristics while removing data that may be personally identifiable to a particular patient. Moreover, the task-based interventional system 65 may incorporate data indicative of costs associated with various outreach/engagement approaches into the modelling, thereby relying on such data as a part of the process for identifying optimal engagement/outreach approaches.

Upon identifying optimal engagement/outreach approaches for a particular patient, the task-based interventional system 65 may be configured to calculate a weighted risk probability of engaging, for example, by evaluating a probability that a patient will engage in the outreach approach and to close a corresponding gap in care. The evaluation may be performed in light of indicating data that calculates the marketing response rate and ability to close a gap in care via outreach. Moreover, the task-based interventional system 65 may execute a historical trend analysis to assess engagement/campaign performance overall, which may be indicative of whether a particular engagement activity is likely to be more/less effective with a particular patient as compared with historical success rates with the same patient. The task-based interventional system 65 may additionally utilize machine-learning based models (e.g., time-series based anomaly detection, regression modelling (e.g., Bayesian modelling, Linear modelling, Neural Network modelling, and/or the like), clustering, and/or the like) to identify the best performing patients and/or payers with respect to various outreach/engagement activities. The overall weighted risk score of the probability that the patient is likely to engage with a particular outreach activity may be generated in the form of a score generated via appropriate machine-learning based models. Data indicative of the identified best performing patients and/or providers may be utilized to determine an action item and/or appropriate channel of communication for closing a gap in care for one or more patients, based at least in part on a determined likelihood of closing a gap in care.

As indicated in Blocks 716-718, the task-based interventional system 65 may increase or decrease the care score associated with a gap in care and/or a particular action item based at least in part on a patient's propensity to engage with various outreach activities. For example, upon determining that the patient has a low propensity to engage, the care score may be decreased, indicating a lower priority of intervening with the gap in care (e.g., a determination that an intervention may be futile). Upon determining that the patient has a high propensity to engage, the care score may be increased, indicating a higher priority of intervening with the gap in care (e.g., a determination that an intervention may be effective in encouraging the patient to close a gap in care). If a patient's propensity to engage is determined to be moderate, the care score may remain unchanged. Determinations of whether a patient has a high, moderate, or low propensity of engaging may be determined based on a generated score indictive of the propensity of a patient to engage with engagement/outreach approaches. A score below a defined threshold may be indicated as a low propensity to engage; a score falling between high and low thresholds may be indicated as a moderate propensity to engage; and a score exceeding a high threshold may be indicated as a high propensity to engage.

Additional characteristics of a gap in care may further influence the resulting care score relevant to the gap in care in accordance with certain models of various embodiments. Moreover, although the concepts reflected in Blocks 702-718 are discussed in reference to the order in which they are shown in FIGS. 7A-7B, it should be understood that certain steps may be performed in a different order than that shown in the figures without departing from the scope of the present disclosure.

As shown at Block 719, the task-based interventional system 65 is configured to calculate care scores. Care scores may be generated for a plurality of entities, such as the patient, one or more relevant providers, the payer, and/or the like. The plurality of care scores may be combined in certain embodiments to generate a cost-adjusted care score. These care scores may be generated based at least in part on the results of various analyses as discussed above, and accordingly the task-based interventional system 65 is configured to consolidate the results of the various models, including the output of a plurality of machine-learning based models and/or a plurality of rule-based models. As just one example, the care scores may be determined by establishing appropriate weighting to be assigned to the output of each applicable model. The weighting to be afforded to the output of each model may be variable and may be based on various characteristics of the output of each model. As an example, for those models generating a substantive output together with a confidence score for the output, the generated weight for the model may be based at least in part on the determined confidence score, with model outputs having higher confidence scores being afforded higher weights when establishing care scores. Moreover, because the outputs of the plurality of models may be non-uniform in formatting and/or content, the generation of care scores may be performed by first translating the outputs of each model into a vector-domain representation, thereby enabling a more direct compilation of data outputs from the plurality of models. The confidence scores associated with these model outputs (if applicable) may be translated into the vector-domain as well, or such confidence scores may be utilized in other models for determining appropriate weights to be afforded to the vector-based representations of the outputs of each model. It should be understood that other models may be utilized for combining the output of various models in other embodiments so as to generate care scores representative of the respective outputs of the plurality of models discussed herein.

Calculation of a patient care score, as reflected in Block 720 and via establishment based at least in part on one or more of the previously discussed processes, provides a longitudinal view of a patient across all gaps in care and corresponding care scores. Accordingly, the patient care score may be calculated in accordance with any of a number of different calculation methodologies. A simple patient care score may be determined by averaging all care scores calculated and attributable to the patient. More complex determinations of patient care scores may generate weighted patient care scores, using machine learning models for example to assign various weights to different care scores calculated and attributable to the patient, considering a relative importance of these care scores.

Examples of patient care scores are illustrated in FIG. 8A, which illustrates those patient care scores as a part of a relational table providing informational links between a patient's unique identifier, a patient's name, a provider associated with the patient (e.g., a patient's primary care provider), a provider medical group, and a patient's care score.

Calculation of a provider care score, as reflected in Block 721 and via establishment based at least in part on one or more of the previously discussed processes, provides an indication of how many patients the provider has associated with a particular plan, and/or how are gaps in care being closed by the provider. Accordingly, the provider care score may be calculated in accordance with any of a number of different calculation methodologies. A simple provider care score may be determined by averaging all care scores calculated and attributable to the provider. More complex determinations of provider care scores may generate weighted provider care scores, using machine learning models for example to assign various weights to different care scores calculated and attributable to the provider, considering a relative importance of these care scores. In yet other examples, a provider care score may be calculated based on updated gap in care scores calculated after the gap in care has been closed (or after a predefined period of time has elapsed without closure of the gap in care), thereby indicating an effectiveness of the provider at closing a gap in care.

Examples of provider care scores are illustrated in FIG. 8B, which illustrates those provider care scores as a part of a relational table providing informational links between a provider's name, a provider's medical group, a plan attributable to the provider (e.g., a CMS contract identifier), a measure associated with the provider, and a provider's care score.

Calculation of a payer care score, as reflected in Block 722 and via establishment based at least in part on one or more of the previously discussed processes, provides an overall payer dashboard that monitors how many patients the payer has associated with a particular plan, and/or how are gaps in care being closed by the payer. Such a payer dashboard may be provided for displaying data indicative of progress towards contract-related goals, such as closing individual patient gaps in care, the financial impact of closing a gap in case, costs associated with outreach/engagement for closing gaps in care, predictions associated with a likelihood achieving contract-goals based on individual patient-specific predictions regarding closing gaps in care, and/or the like. The payer dashboard may additionally comprise various levels of detail for generating reports, such as displaying data indicative of a weighted risk probability for a member, an individual patient's historical probability of self-closing a gap in care, a patient's historical response to outreach, a determined best outreach strategy, a weighted risk probability associated with engaging a patient, and/or the like). Accordingly, the payer care score may be calculated in accordance with any of a number of different calculation methodologies. A simple payer care score may be determined by averaging all care scores calculated and attributable to the payer. More complex determinations of payer care scores may generate weighted payer care scores, using machine learning models for example to assign various weights to different care scores calculated and attributable to the payer, considering a relative importance of these care scores. In yet other examples, a payer care score may be calculated based on updated gap in care scores calculated after the gap in care has been closed (or after a predefined period of time has elapsed without closure of the gap in care), thereby indicating an effectiveness of the payer at closing a gap in care.

Examples of payer care scores are illustrated in FIG. 8C. As shown in FIG. 8C, payer care scores may be determined for individual interventional strategies implemented by various payers. Accordingly, the payer care scores thus illustrate the effectiveness of a payer at providing interventions according to various interventional strategies, to gauge the relative effectiveness (and/or cost effectiveness) of certain interventional strategies. The illustration of FIG. 8C shows the payer care scores calculated for combinations of particular plans (e.g., CMS contract identifiers), measures, and interventional strategies.

Based at least in part on the generated care scores, the task-based interventional system 65 may then determine a cost adjusted care score specific for a particular gap in care. The cost adjusted care score providers payers and/or providers with an understanding of a member level cost-benefit analysis for various gap closure efforts, an attribution of the associated costs to specific entities (e.g., a provider and/or a payer). Thus, a value may be attributable to improving the quality of the patient's care as defined as the ability to correctly report quality measures to plans. As a part of calculating the cost adjusted care score, the task-based interventional system 65 executes a machine-learning model to identify costs of outreach/engagement activities, arranged by patient.

The task-based interventional system 65 may then determine an action item for closing a gap in care, as well as appropriate interventional strategies to be utilized in engaging the patient to encourage closure of the gap in care via the identified action items. This determination of an optimal combination of an action item and invention may be generated based at least in part on a holistic evaluation of all gaps in care across individual patients, providers, and payers and a plurality of known outreach and intervention opportunities reflected within historical data. Such data is utilized as inputs for a machine-learning model to determine an optimal interventional strategy for engaging the patient to close the gap in care. This machine learning model is configured to identify a best intervention strategy, and to determine whether the determined best intervention strategy is to be executed by the provider, the payer, or individually by the patient. The identified optimal intervention strategy may encompass a strategy of no intervention, for example, to close a gap in care that has remained open for an extended period of time, and for which the patient has shown a consistent history of failures to close gaps in care, thereby indicating that any intervention strategy may be futile. As another example, an optimal intervention strategy may encompass a determination that the provider is the best entity to reach out to a particular patient with an intervention that is likely to result in the closure of a particular gap in care. As yet another example, an optimal intervention strategy may encompass a determination that a provider is recommended to perform a housecall on a patient to close multiple gaps in care simultaneously for a particular patient.

e. Task Data Object Generation

As discussed herein, the task-based interventional system 65 is configured to generate a task data object to facilitate an intervention with the patient by automatically initiating a series of a computer-specific processes for presenting data and/or communications to the appropriate entity to facilitate a process of providing the indicated outreach to the patient. As noted herein, the task data object comprises data indicative of an action item necessary for closure of an identified gap in care, and may additionally comprise executable data objects for initializing the generation of data and/or communications to be provided to relevant entities to facilitate the process of providing information indicative of the necessary action item to the patient.

FIG. 7C specifically illustrates steps associated with generation of a task data object. The task data object comprises data indicative of the action item necessary for closure of a particular gap in care for a particular patient, and accordingly Block 725 indicates that action item data representing such data may be populated for inclusion within a task data object. Such data may be embodied as text-based data providing a summary of the necessary steps to be performed by a patient (and/or provider or payer) that is presented for consumption by a payer representative or a provider. In other embodiments, such data may be presented as human-readable (e.g., text-based) data in the form of a desired actor-specific action item providing detailed instructions (or short instructions) of the necessary steps to be performed by the patient (and/or provider or payer) that is provided for presentation directly to the patient, for example, as a part of an electronic intervention campaign (e.g., to be provided via email, text message, via social media, and/or the like), a mailer-based intervention campaign, and/or the like. It should be understood that the data indicative of the action item may be presented in the form of an audio-file (e.g., to be utilized during certain electronic-based interventions with the patient, such as telephonic intervention campaigns), a video-file, a calendar data object (e.g., configured to be imported into a patient's computer-based calendaring program), a hyperlink (e.g., providing a link to a fillable form or other electronic resource provided for patient review), and/or the like. The data indicative of the appropriate action item may be generated and/or selected from a database based at least in part on the result of the gap in care analysis process as discussed above for identifying a next best action (inclusive of an action item for the patient) based on a plurality of analytical considerations for addressing a gap in care. The data to be included within the task data object may directly comprise at least a portion of the output of the above-described analysis, or the data to be included within the task data object may be retrieved from an appropriate storage location based at least in part on an identifier or other reference data included within the output of the above analysis. As a specific example, the output of the above analysis may comprise data identifying an appropriate action item for the patient, and such data may be utilized to retrieve a textual summary (or other data type) of the action item from a database for inclusion with interventional communications to be provided to the patient.

As noted, the task data object may additionally comprise an executable data object configured for initializing one or more computer-based processes to facilitate an intervention with the patient. Accordingly, Block 726 represents the generation of an appropriate executable data object for inclusion within the task data object. In certain embodiments, the executable data object is embodied as a data object configured to automatically generate and/or transmit a communication to a particular relevant entity to provide the data indicative of the action item needed for the patient, thereby providing the relevant individual with the necessary information to intervene with the patient. As a non-limiting example, the communication may be embodied as an automatically generated email, an automatically generated audio-based communication, an automatically generated text-message, and/or the like. In other embodiments, the executable data object may be embodied as an executable data object configured to initialize a workflow software system operating on and/or accessible by a particular entity's computing system. As an example, a workflow system may comprise an Electronic Medical Record (EMR) system, an Electronic Health Record (EHR) system, a calendaring system, a project management system, a work scheduler system, and/or the like, that is operable on or accessible via a provider's computing system.

As indicated at Block 727, the task data object comprises entity data populated to identify an appropriate entity for performing an intervention with the patient (e.g., a provider, a payer representative, and/or the like, which may be identified by a unique identifier correlated with a corresponding profile stored within the data store). Utilizing data identifying an appropriate entity for performing the intervention, the task-based interventional system 65 may retrieve data indicative of an appropriate communication channel to utilize to communicate with the appropriate entity (e.g., by referencing communication-specifying data within a corresponding profile). The task-based interventional system 65 may thus configure the executable data object within the task data object to initialize appropriate communications between the task-based interventional system 65 and the relevant entity. For example, upon determining that communications with a provider should be accomplished via email, the task-based interventional system 65 may configure the executable data object of the task data object to generate an email providing relevant data to the provider. As another example, upon determining that communications with a payer representative should be accomplished by adding a workflow data object within a workflow software system corresponding with the representative (e.g., the workflow data object requesting the payer representative generate a mailer to be provided to the patient), the task-based interventional system 65 generates an appropriate executable data object configured to communicate with the relevant workflow system (e.g., via an API or other communications interface) to provide appropriate data to the workflow software system to cause the workflow software system to generate the workflow data object as indicated. This appropriate executable data object may be generated at least in part on a determined appropriate interface to provide data to the workflow software, such that data is appropriately provided to the workflow software for providing data indicative of the action item to the patient.

Although illustrated in a particular order, it should be understood that the steps reflected within Blocks 725-727 may be performed in any order. The data generated and/or populated for the task data object is consolidated into the task data object as indicated at Block 728 for execution thereof.

In certain embodiments, data indicative of the generation of the task data object may be stored within a data store for later retrieval, for archive purposes, as an indication of prior interventions, and/or the like. In certain embodiments, a copy of the task data object may be stored within a data store. In other embodiments, a compressed task data object may be stored. Other indications of task data objects, such as data hashes, may be stored in other embodiments. Moreover, in certain embodiments the stored data indicative of the task data object may be updated (e.g., periodically, upon the occurrence of a trigger event, and/or the like) to reflect the effectiveness of the intervention reflected by the task data object. Such data may be utilized as historical data in later analyses as indicative of successes and/or failures in utilizing various interventional strategies with certain patients, providers, and/or payers. Accordingly, such data may be stored with links or other associations to certain profiles, such as patient profiles, provider profiles, payer profiles, and/or the like, such that the stored data may be appropriately considered during later analyses relevant to particular entities.

f. Task Data Object Execution

As noted above, the task data object may be executed (as indicated at Block 729) to facilitate an intervention with a patient to close a gap in care. The task-based interventional system 65 may be configured to generate task data objects based at least in part on the results of the analytical process discussed above. Accordingly, certain embodiments may be configured to generate task data objects upon determining that an intervention is likely to be successful with a particular patient. Thus, rather than generating task data objects upon determining that an intervention is likely to be futile, the task-based interventional system 65 may be configured to generate data indicating that a task data object has not been generated for the intervention, and may populate the data with information indicating why the task data object was not generated, for example, for later audit purposes, for later analytical purposes (e.g., as historical data), and/or the like.

However, when a task data object has been generated, the task-based interventional system 65 is configured to execute the task data object at an appropriate time. For example, the task data object may be executed immediately upon generation, or the task data object may be stored and executed at a defined later time after generation.

Upon execution of the task data object, the task-based interventional system 65 is configured to provide appropriate data to an indicated entity (e.g., a provider, a payer representative, and/or the like) to engage the patient to provide relevant details of action items to close a particular gap in care. The task-based interventional system 65 may additionally generate, as a part of execution of the task data object, an entry within a data store corresponding to the generated task data object, wherein the entry is configured for storing data indicative of actions taken with respect to the action item. For example, the entry may comprise a data log indicating various actions occurring with respect to a particular task data object, as well as timestamps associated with each executed action. As an example, a data log may indicate when the task data object was generated, when it was first initialized, when the task-based interventional system 65 received data indicating that a relevant entity reached out to the patient, when (and/or how) the patient responded to the intervention, and/or the like. The entry within the data store may be indicative of historical data that may be associated with (e.g., via relational links within the data store) one or more profiles, such as a patient profile, a provider profile, a payer profile, and/or the like. The data entry may comprise a unique indicator that may reflect an analogous indicator stored (e.g., as metadata) within the task data object, such that later updates relating to the task data object may be appropriately linked with the database entry, thereby enabling accurate monitoring of the effectiveness of a task data object and for generation of an accurate and complete database of historical data that may be utilized in the above-mentioned machine-learning models.

In certain embodiments, an entry corresponding to a particular action item may be generated even upon determining that an intervention is likely futile or unnecessary. Such data entries may reflect that the analysis discussed above determined that an intervention would be futile (e.g., the patient is not likely to close the gap in care regardless of intervention); or such data entries may reflect that the analysis discussed above determined that an intervention is unnecessary (e.g., the patient is likely to close the gap in care without an intervention). Accordingly, such data entries may be provided as historical data entries that may be populated with additional data indicating whether such initial analytical conclusions were correct (e.g., indicating whether a patient self-closed a gap in care; indicating whether low-cost interventions performed despite an initial conclusion were successful), such that the historical data may reflect an indication of the accuracy of the initial results of the analytical process discussed above, which may be utilized for future analyses.

IV. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A computer-implemented task-based interventional system comprising:
one or more non-transitory memory storage areas;
one or more processors configured to:
receive claims data relating to a patient, wherein the claims data comprises (a) a plurality of claim data objects each identifying previously executed actions and (b) data identifying at least one program;
based at least in part on the at least one program, apply rule-based criteria for determining whether the claims data relating to the patient reflects one or more gaps in care relating to the at least one program, wherein each of the one or more gaps in care is reflected as an unfulfilled action item that is not satisfied by the plurality of claim data objects;
output, based at least in part on the rule-based criteria, criteria for closing the one or more gaps in care;
generate, by executing one or more machine learning models, predicted care scores for one or more available action items, wherein the one or more available action items generate data to close the one or more gaps in care;
identify, based at least in part on the predicted care scores and from the one or more available action items, a first action item to generate data that closes the one or more gaps in care;
generate a task data object for initiation of the first action item, wherein the task data object comprises:
at least one actor identifier indicating a communication address of an individual for executing at least a portion of the first action item;

a desired actor-based action item comprising a human-readable indication of the desired actor-based action item to generate data to close the one or more gaps in care;

data identifying at least one computer-based communication protocol for providing communication between the computer-implemented task-based interventional system and the communication address; and an executable job for execution at least partially by the computer- implemented task-based interventional system to provide the communication to the communication address of the individual, in accordance with the at least one computer-based communication protocol; and execute the executable job to provide at least the desired actor-based action item of the task data object to an external computing entity. .

2. The computer-implemented task-based interventional system of claim 1, wherein executing one or more machine-learning models to generate care scores comprises:

evaluating historical data corresponding to each of a plurality of actors to generate a care score corresponding to each of the plurality of actors indicating a likelihood of each of the plurality of actors to complete desired actor-based action items.

3. The computer-implemented task-based interventional system of claim 1, wherein the one or more processors are further configured to generate a user interface providing a populated listing of gaps in care relating to the at least one program.

4. The computer-implemented task-based interventional system of claim 1, wherein executing the executable job comprises causing a workflow software system to populate a workflow data object.

5. The computer-implemented task-based interventional system of claim 1, wherein identifying the first action item to close a gap in care comprises:

generating care scores for each of a plurality of entities; and identifying the first action item via a machine-learning model based at least in part on generated care scores for each of the plurality of entities.

6. The computer-implemented task-based interventional system of claim 5, wherein generating the care scores for the plurality of entities comprises:

determining a patient care score based at least in part on historical data indicative of historical actions of the patient;

determining a provider care score for a relevant care provider associated with the patient, wherein the provider care score is determined based at least in part on historical data associated with the relevant care provider; and determining a payer care score indicative of one or more interventional strategies historically implemented by a payer associated with the patient.

7. A computer-implemented method for generating a computer-based intervention to close gaps in care in stored claims data, the method comprising:

receiving, via one or more processors, claims data relating to a patient, wherein the claims data comprises (a) a plurality of claim data objects each identifying previously executed actions and (b) data identifying at least one program;

based at least in part on the at least one program, applying, via the one or more processors, rule-based criteria for determining whether the claims data relating to the patient reflects one or more gaps in care relating to the at least one program, wherein each of the one or more gaps in care is reflected as an unfulfilled action item that is not satisfied by the plurality of claim data objects;

generating, via the one or more processors, output based at least in part on the rule-based criteria, criteria for closing the one or more gaps in care;

generating, by executing one or more machine learning models via the one or more processors, predicted care scores for one or more available action items, wherein the one or more available action items generate data to close the one or more gaps in care;

identifying, via the one or more processors and based at least in part on the predicted care scores and from the one or more available action items, a first action item to generate data that closes the one or more gaps in care;

generating, via the one or more processors, a task data object for initiation of the first action item, wherein the task data object comprises:

at least one actor identifier indicating a communication address of an individual for executing at least a portion of the first action item;

a desired actor-based action item comprising a human-readable indication of the desired actor-based action item to generate data to close the one or more gaps in care;

data identifying at least one computer-based communication protocol for providing communication between the one or more processors and the communication address; and an executable job for execution at least partially by the one or more processors to provide the communication to the communication address of the individual, in accordance with the at least one computer-based communication protocol; and executing, via the one or more processors, the executable job to provide at least the desired actor-based action item of the task data object to an external computing entity.

8. The computer-implemented method of claim 7, wherein executing one or more machine-learning models to generate care scores comprises:

evaluating historical data corresponding to each of a plurality of actors to generate a care score corresponding to each of the plurality of actors indicating a likelihood of each of the plurality of actors to complete desired actor-based action items.

9. The computer-implemented method of claim 7, further comprising generating a user interface providing a populated listing of gaps in care relating to the at least one program.

10. The computer-implemented method of claim 7, wherein executing the executable job comprises causing a workflow software system to populate a workflow data object.

11. The computer-implemented method of claim 7, wherein identifying the first action item to close a gap in care comprises:

generating care scores for each of a plurality of entities; and identifying the first action item via a machine-learning model based at least in part on generated care scores for each of the plurality of entities.

12. The computer-implemented method of claim 11, wherein generating the care scores for the plurality of entities comprises:
- determining a patient care score based at least in part on historical data indicative of historical actions of the patient;
- determining a provider care score for a relevant care provider associated with the patient, wherein the provider care score is determined based at least in part on historical data associated with the relevant care provider; and
- determining a payer care score indicative of one or more interventional strategies historically implemented by a payer associated with the patient.

13. A non-transitory computer-readable storage medium having program code embedded thereon, the program code executable on a processor of a computer system to perform processes for:
- receiving claims data relating to a patient, wherein the claims data comprises (a) a plurality of claim data objects each identifying previously executed actions and (b) data identifying at least one program;
- based at least in part on the at least one program, applying a rule-based criteria for determining whether the claims data relating to the patient reflects one or more gaps in care relating to the at least one program, wherein each of the one or more gaps in care is reflected as an unfulfilled action item that is not satisfied by the plurality of claim data objects;
- generating output from based at least in part on the rule-based criteria, criteria for closing the one or more gaps in care;
- generating, by executing one or more machine learning models, predicted care scores for one or more available action items, wherein the one or more available action items generate data to close the one or more gaps in care;
- identifying, based at least in part on the predicted care scores and from the one or more available action items, a first action item to generate data that closes the one or more gaps in care;
- generating a task data object for initiation of the first action item, wherein the task data object comprises:
  - at least one actor identifier indicating a communication address of an individual for executing at least a portion of the first action item;
  - a desired actor-based action item comprising a human-readable indication of the desired actor-based action item;
  - data identifying comprising at least one computer-based communication protocol for providing communication to the communication address; and
  - an executable job for execution to provide the communication to the communication address of the individual, in accordance with the at least one computer-based communication protocol; and
- executing the executable job to provide at least the desired actor-based action item of the task data object to an external computing entity.

14. The non-transitory computer-readable storage medium of claim 13, wherein executing one or more machine-learning models to generate care scores comprises:
- evaluating historical data corresponding to each of a plurality of actors to generate a care score corresponding to each of the plurality of actors indicating a likelihood of each of the plurality of actors to complete desired actor-based action items.

15. The non-transitory computer-readable storage medium of claim 13, further comprising generating a user interface providing a populated listing of gaps in care relating to the at least one program.

16. The non-transitory computer-readable storage medium of claim 13, wherein executing the executable job comprises causing a workflow software system to populate a workflow data object.

17. The non-transitory computer-readable storage medium of claim 13, wherein identifying the first action item to close a gap in care comprises:
- generating care scores for each of a plurality of entities; and
- identifying the first action item via a machine-learning model based at least in part on generated care scores for each of the plurality of entities.

18. The non-transitory computer-readable storage medium of claim 13, wherein generating the care scores for a plurality of entities comprises:
- determining a patient care score based at least in part on historical data indicative of historical actions of the patient;
- determining a provider care score for a relevant care provider associated with the patient, wherein the provider care score is determined based at least in part on historical data associated with the relevant care provider; and
- determining a payer care score indicative of one or more interventional strategies historically implemented by a payer associated with the patient.

* * * * *

UNITED STATES PATENT AND TRADEMARK OFFICE
CERTIFICATE OF CORRECTION

| | |
|---|---|
| PATENT NO. | : 11,574,731 B2 |
| APPLICATION NO. | : 16/904313 |
| DATED | : February 7, 2023 |
| INVENTOR(S) | : Scott D. Johnson et al. |

It is certified that error appears in the above-identified patent and that said Letters Patent is hereby corrected as shown below:

In the Claims

In Column 37, Claim 13, Line 30, delete "output from based" and insert -- output based --, therefor.

Signed and Sealed this
Second Day of May, 2023

Katherine Kelly Vidal
Director of the United States Patent and Trademark Office